US008389253B2

(12) United States Patent
Diner et al.

(10) Patent No.: US 8,389,253 B2
(45) Date of Patent: Mar. 5, 2013

(54) ORGANIC SOLVENT PRETREATMENT OF BIOMASS TO ENHANCE ENZYMATIC SACCHARIFICATION

(75) Inventors: Bruce A Diner, Chadds Ford, PA (US); Janine Fan, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/539,555

(22) Filed: Jul. 2, 2012

(65) Prior Publication Data

US 2012/0264173 A1   Oct. 18, 2012

Related U.S. Application Data

(62) Division of application No. 12/639,033, filed on Dec. 16, 2009, now Pat. No. 8,241,880.

(60) Provisional application No. 61/139,147, filed on Dec. 19, 2008.

(51) Int. Cl.
| | |
|---|---|
| *C12P 7/06* | (2006.01) |
| *C12P 19/00* | (2006.01) |
| *C12P 7/64* | (2006.01) |
| *C12P 7/62* | (2006.01) |
| *C12P 7/40* | (2006.01) |
| *C12P 7/02* | (2006.01) |
| *C12P 7/04* | (2006.01) |
| *C12P 7/18* | (2006.01) |
| *C12P 7/16* | (2006.01) |
| *C07H 1/08* | (2006.01) |

(52) U.S. Cl. .......... 435/161; 435/72; 435/106; 435/134; 435/135; 435/136; 435/155; 435/157; 435/158; 435/160; 536/128

(58) Field of Classification Search .................... 435/72, 435/128, 134, 135, 136, 155, 157, 158, 160, 435/106, 161; 536/128
See application file for complete search history.

(56) References Cited

U.S. PATENT DOCUMENTS

| | | | |
|---|---|---|---|
| 2,218,479 | A | 10/1940 | Peterson et al. |
| 3,490,993 | A | 1/1970 | Fisher et al. |
| 4,178,861 | A | 12/1979 | Vandernoek et al. |
| 4,329,200 | A | 5/1982 | Sarkanen |
| 4,470,851 | A | 9/1984 | Paszner et al. |
| 4,597,830 | A | 7/1986 | April et al. |
| 5,554,520 | A | 9/1996 | Fowler et al. |
| 2004/0231060 | A1 | 11/2004 | Burdette et al. |
| 2008/0202504 | A1 | 8/2008 | Hilst |

FOREIGN PATENT DOCUMENTS

| | | |
|---|---|---|
| DE | 3506108 A1 | 8/1986 |
| WO | 9429475 A1 | 12/1994 |
| WO | 2004081185 A2 | 9/2004 |
| WO | 2007/051269 A1 | 5/2007 |

OTHER PUBLICATIONS

Arato, Claudio et al., The Lignol Approach to Biorefining of Woody Biomass to Produce Ethanol and Chemicals, Applied Biochemistry and Biotechnology, 2005, pp. 871-882, vol. 121-124, Humana Press Inc.
Mosier, Nathan et al., Features of promising technologies for pretreatment of lignocellulosic biomass, Bioresource Technology, 2005, pp. 673-686, vol. 96, Elsevier Ltd.
Pan, Xuejun et al., Bioconversion of Hybrid Poplar to Ethanol and Co-Products Using an Organosolv Fractionation Process: Optimization of Process Yields, Biotechnology and Bioengineering, Aug. 5, 2006, pp. 851-861, vol. 94, No. 5, Wiley Periodicals, Inc.
Wyman, Charles E. et al., Comparative sugar recovery data from laboratory scale application of leading pretreatment technologies to corn stover, Bioresource Technology, 2005, pp. 2026-2032, vol. 96, Elsevier Ltd.
Lee, Yong-Hyun et al., Evaluation of Organosolv Processes for the Fractionation and Modification of Corn Stover for Bioconversion, Biotechnology and Bioengineering, 1987, pp. 572-581, vol. 29, John Wiley & Sons, Inc.
Peter, Siegfried et al., Degradation of Lignin with Monomethylamine, Chemical Engineering Technology, 1992, pp. 213-217, vol. 15.
Wyman, Charles E., Coordinated development of leading biomass pretreatment technologies, Bioresource Technology, 2005, pp. 1959-1966, vol. 96, Elsevier Ltd.
Kleinert, Theodor N., Organosolv pulping with aqueous alcohol, Tappi, Aug. 1974, pp. 99-102, vol. 57, No. 8.
Park, Jung-Keug et al., Ammonia Catalyzed Organosolv Delignification of Poplar, Chemical Engineering Communications, 1988, pp, 187-205, vol. 65.
Hsu, Teh-An, Pretreatment of Biomass, Handbook on Bioethanol: Production and Utilization, Charles E. Wyman , Ed., 1996, pp, 179-212, Taylor and Francis.
International Search Report dated Mar. 8, 2010, International Application No. PCT/US2009/068224.

*Primary Examiner* — Herbert J Lilling

(57) ABSTRACT

Biomass is pretreated using an organic solvent solution under alkaline conditions in the presence of one or more alkylamine and optionally one or more additional nucleophile to fragment and extract lignin. Pretreated biomass is further hydrolyzed with a saccharification enzyme consortium. Fermentable sugars released by saccharification may be utilized for the production of target chemicals by fermentation.

19 Claims, 6 Drawing Sheets

ORGANIC SOLVENT PRETREATMENT OF BIOMASS TO ENHANCE ENZYMATIC SACCHARIFICATION

The application claims the benefit of U.S. Provisional Application No. 61/139,147, filed Dec. 19, 2008, the disclosure of which is hereby incorporated in its entirety.

FIELD OF THE INVENTION

Methods for producing readily saccharifiable carbohydrate-enriched lignocellulosic biomass are provided. Specifically, pretreated biomass is prepared through simultaneous fragmentation and selective extraction of lignin in an organic solvent solution under alkaline conditions at elevated temperatures in the presence of one or more alkylamine and various nucleophiles. The remaining carbohydrate-enriched solids in the pretreated biomass may then be subjected to enzymatic saccharification to obtain fermentable sugars, which may be subjected to further processing for the production of target products.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of cellulose, hemicellulose, pectins and of lignin are generally treated by a variety of chemical, mechanical and enzymatic means to release primarily hexose and pentose sugars, which can then be fermented to useful products.

Pretreatment methods are often used to make the polysaccharides of lignocellulosic biomass more readily accessible to cellulolytic enzymes. One of the major impediments to cellulolytic enzyme digest is the presence of lignin, a barrier that limits the access of the enzymes to their substrates, and a surface to which the enzymes bind non-productively. Because of the significant costs associated with enzymatic saccharification, it is desirable to minimize the enzyme loading by either inactivation of the lignin to enzyme adsorption or its outright extraction. Another challenge is the inaccessibility of the cellulose to enzymatic hydrolysis either because of its protection by hemicellulose and lignin or by its crystallinity. Pretreatment methods that attempt to overcome these challenges include: steam explosion, hot water, dilute acid, ammonia fiber explosion, alkaline hydrolysis (including ammonia recycled percolation), oxidative delignification and organosolv.

Organosolv methods, as previously practiced for the treatment of lignocellulose biomass, for either the production of pulp or for biofuels applications, while generally successful in lignin removal, have suffered from poor sugar recoveries, particularly of xylose. For example, the use of slightly acidic ethanol-water mixtures (e.g., EtOH 42 weight %) at elevated temperature to remove lignin from lignocellulosic biomass (Kleinert, T. N., Tappi, 57: 99-102, 1974) resulted in substantial loss of carbohydrate. Dilute acid hydrolysis at 95° C. followed by organic solvent extraction and enzymatic saccharification (Lee, Y-H. et al., Biotech. Bioeng., 29: 572-581, 1987) resulted in substantial loss of hemicellulose during hydrolysis, additional carbohydrate loss upon organic solvent extraction and poor yield (~50% of total carbohydrate) upon enzymatic saccharification of residue. Use of aqueous organic solvent containing ammonia at elevated temperatures to treat lignocellulosic biomass (Park J.-K. and Phillips, J. A., Chem. Eng. Comm. 65: 187-205, 1988) required the use of a high liquid to solids ratio in pretreatment and resulted in substantial loss of hemicellulose and poor enzymatic saccharification of cellulose. Treatment of biomass with gaseous water and methylamine followed by extraction with organic solvent and then extraction with water, required three steps and resulted in a substantial loss of carbohydrate (Siegfried, P. and Götz, R., Chem. Eng. Technol., 15: 213-217, 1992). Treatment with polyamines or ethylamine in water-aliphatic alcohol mixtures plus catalyst at elevated temperature required high liquid/solids ratio and low concentrations of alcohol led to poor sugar recovery, particularly of xylan (U.S. Pat. No. 4,597,830A). Thioglycolate in aqueous alkaline solution used to treat lignocellulosic biomass at elevated temperature, followed by a hot water wash required use of alkali-metal or alkaline-earth hydroxides. This method requires the costly disposal of inorganic ions, high weight % thioglycolate, and use of large volumes of water (U.S. Pat. No. 3,490, 993). Treatment with organic solvent-water mixtures in the presence of sulfide/bisulfide at elevated temperatures required a high solvent/solids ratio and elevated sulfur content and resulted in a substantial loss of carbohydrate, (U.S. Pat. No. 4,329,200).

Additional shortcomings of previously applied methods include, separate hexose and pentose streams (e.g. dilute acid), inadequate lignin extraction or lack of separation of extracted lignin from polysaccharide, particularly in those feedstocks with high lignin content (e.g., sugar cane bagasse, softwoods), disposal of waste products (e.g., salts formed upon neutralization of acid or base), and poor recoveries of carbohydrate due to breakdown or loss in wash steps. Other problems include the high cost of energy, capital equipment, and pretreatment catalyst recovery, and incompatibility with saccharification enzymes.

One of the major challenges of biomass pretreatment is to maximize the extraction or chemical neutralization (with respect to non-productive binding of cellulolytic enzymes) of the lignin while minimizing the loss of carbohydrate (cellulose plus hemicellulose) via low-cost, efficient processes. The higher the selectivity, the higher the overall yield of monomeric sugars following combined pretreatment and enzymatic saccharification.

In this disclosure, organosolv-mediated fragmentation and selective extraction of lignin at elevated temperatures under alkaline conditions in combination with one or more alkylamine and optionally various nucleophiles is used, in a cost-effective process, to produce carbohydrate-enriched biomass that is highly susceptible to enzymatic saccharification, producing very high yields of fermentable sugars (glucose, as well as xylose) for bioconversion to target products (e.g., value-added chemicals and fuels). Surprisingly, use of alkylamines in the present disclosure resulted in significantly improved lignin fragmentation and extraction and high carbohydrate retention.

SUMMARY OF THE INVENTION

The present invention provides a method for producing readily saccharifiable carbohydrate-enriched biomass and for selectively extracting lignin from lignocellulosic biomass while nearly quantitatively retaining carbohydrate. The methods include treating lignocellulosic biomass with an organic solvent solution, such as organosolv, and one or more alkylamines under alkaline conditions at elevated temperatures in a single step. In certain embodiments the solvent solution further comprises additional nucleophilic components such as, ammonia, thiols, and sulfides. Following pretreatment, the biomass may be further treated with a saccharification enzyme consortium to produce fermentable sugars. These sugars may be subjected to further processing for the production of target products.

Accordingly, the invention provides a method for producing carbohydrate-enriched biomass comprising:
(a) providing lignocellulosic biomass comprising lignin;
(b) suspending the biomass of (a) in an organic solvent solution comprising water and one or more alkylamines under alkaline conditions whereby a biomass-solvent suspension is formed;
(c) heating the biomass-solvent suspension to a temperature of about 100° C. to about 220° C. for about 5 minutes to about 5 hours whereby lignin is fragmented and is dissolved in the suspension; and
(d) filtering free liquid whereby the dissolved lignin is removed and whereby carbohydrate-enriched biomass is produced.

Particularly suitable alkylamines include those selected from the group consisting of $R-NH_2$, $R_2-NH$, $R_3N$, $(H_2N-R-NH_2)$, $(H_2N-R(NH_2)_2)$, $(HO-R-NH_2)$, $((HO)_2-R-NH_2)$, $(HO-R-(NH_2)_2)$, $(HS-R-NH_2)$, $((HS)_2-R-NH_2)$, $(HS-R-(NH_2)_2)$ and $(H_2N-R(OH)(SH))$ and combinations thereof, wherein R is independently a monovalent, divalent or trivalent 1-6 carbon alkane, alkene or alkyne, linear, cyclic or branched.

Particularly suitable feedstocks for use in the methods of the invention include but are not limited to switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

In another embodiment the invention provides A method of simultaneous fragmentation and selective extraction of lignin from lignocellulosic biomass to produce a substantially lignin-free biomass, the method comprising the steps of:
(a) providing:
1) an amount of lignocellulosic biomass;
2) a multi-component solvent solution comprising from about 40% to about 70% ethanol in water; and
3) one or more alkylamines under alkaline conditions;
(b) contacting said biomass with the multi-component solvent solution of (a) to form a solvent-biomass mixture;
(c) placing the solvent-biomass mixture in a sealed pressure vessel whereby the mixture of (b) is heated at a temperature of about 100° C. to about 220° C. for about 5 to about 5 hours whereby lignin is fragmented and dissolved in the solvent; and
(d) removing the dissolved lignin of (c) by filtration and
(e) washing the residual biomass with organic solvent, whereby substantially lignin-free biomass is produced.

BRIEF DESCRIPTION OF THE FIGURES

FIG. 1B shows xylose monomer yield during the time course of enzymatic saccharification in the presence and absence of 1% Tween 20 (w/v) following pretreatment at 187° C. for 1 hour in 70% EtOH in $H_2O$ (v/v) and 14% methylamine (w/w biomass) with or without 2% thioglycolate (w/w biomass).

FIG. 2B shows the UV absorbance spectra of filtrates (diluted 1:5000 with 70% EtOH in $H_2O$ (v/v)) following pretreatment at 187° C. in 70% EtOH in $H_2O$ (v/v) plus 14% methylamine (w/w biomass) and with 14% methylamine (w/w biomass) plus 2% glycolic acid (w/w biomass) or 2% glycine (w/w biomass).

FIG. 3B—shows the UV absorbance spectra of filtrates (diluted 1:5000 with 70% EtOH in $H_2O$ (v/v)) following pretreatment at 187° C. for 1 h in 70% EtOH in $H_2O$ (v/v) plus 14% methylamine (w/w biomass) with or without 2% elemental sulfur (w/w biomass).

DETAILED DESCRIPTION OF THE INVENTION

Figure 1A:
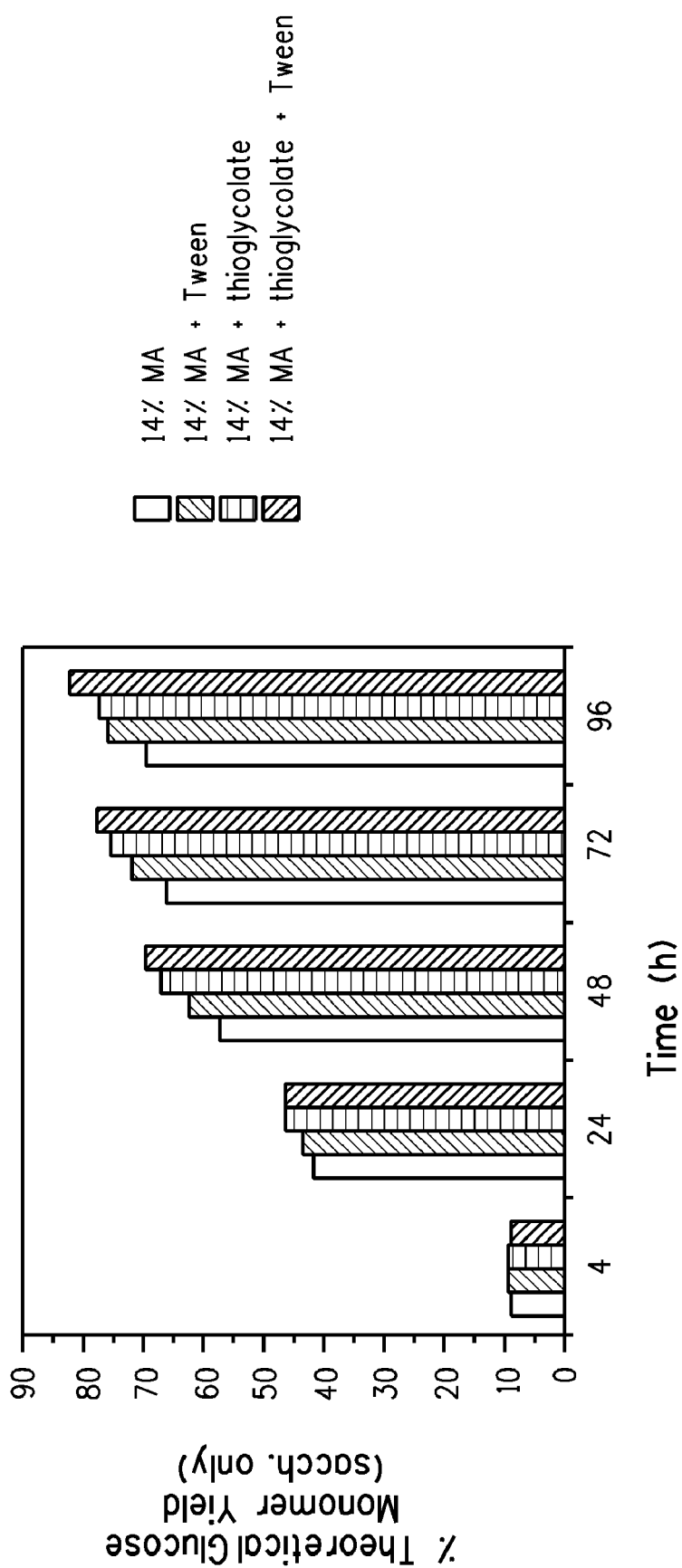
FIGS. 1A and 1B—FIG. 1A shows glucose monomer yield during the time course of enzymatic saccharification in the presence and absence of 1% Tween 20 (w/v) following pretreatment at 187° C. for 1 hour in 70% EtOH in $H_2O$ (v/v) and 14% methylamine (w/w biomass) with or without 2% thioglycolate (w/w biomass)

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a process for the treatment of biomass in order to produce readily saccharifiable carbohydrate-enriched biomass to enhance the subsequent enzymatic saccharification step such that readily fermentable sugars can be obtained from saccharification.

A process involving a pretreatment step wherein lignin is simultaneously fragmented and extracted using an organic solvent under alkaline conditions at elevated temperatures in the presence of one or more alkylamine is employed. Additional nucleophiles may be employed for further benefit. The treated biomass is then filtered and washed to remove solubilized lignin, acetic acid, acetamides, alkylamides and excess reagent and then digested with a saccharification enzyme consortium to produce readily fermentable sugars. The sugars may then be further processed to one or more target product. The removed lignin may also be further processed and utilized for other purposes (such as burning for energy) to increase efficiency.

Definitions

The following definitions are used in this disclosure:

"Room temperature" and "ambient" when used in reference to temperature refer to any temperature from about 15° C. to about 25° C.

"Fermentable sugars" refers to a sugar content primarily comprising monosaccharides and some disaccharides that can be used as a carbon source by a microorganism (some polysaccharides may be present) in a fermentation process to produce a target product. "Readily fermentable sugars" means that additional costly processing is not necessary and/or that a fermentative microorganism can be contacted with the resulting sugars with minimal impediments from inhibitors or other components that may adversely affect fermentation.

"Lignocellulosic" refers to material comprising both lignin and cellulose. Lignocellulosic material may also comprise hemicellulose. In the processes described herein, lignin is dissolved and substantially removed from the lignocellulosic biomass to produce a carbohydrate-enriched biomass.

"Dissolved lignin" as referred to herein means the lignin that is dissolved in an organic solvent solution.

"AI lignin" refers to acid-insoluble lignin.

"Autohydrolysis" refers to the hydrolysis of biomass in the presence of solvent (water or organic solvent plus water) plus heat with no further additions, such as without exogenous acid or base or hydrolytic enzyme addition.

"Cellulosic" refers to a composition comprising cellulose.

"Target product" refers to a chemical, fuel, or chemical building block produced by fermentation. Product is used in a broad sense and includes molecules such as proteins, including, for example, peptides, enzymes and antibodies. Also contemplated within the definition of target product are ethanol and butanol.

"Dry weight of biomass" refers to the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

"Selective extraction" means removal of lignin while substantially retaining carbohydrates.

"Solvent solution" and "organic solvent solution", as used herein, is an organic solvent mixture in water that includes any organic liquid that dissolves a solid, liquid, or gaseous solute, resulting in a solution. The most suitable solvent solutions for this invention are organic solvents such as ethanol, methanol, n-propanol, isopropanol, n-butanol, 2-butanol, isobutanol, t-butanol, pentanol and hexanol and diols with the same number of carbons. They can also include aprotic solvents. The solvent solutions can include additional components in mixture with the solution, e.g, the solvent solution may include one or more nucleophile.

"Biomass" and "lignocellulosic biomass" as used herein refer to any lignocellulosic material, including cellulosic and hemi-cellulosic material, for example, bioenergy crops, agricultural residues, municipal solid waste, industrial solid waste, yard waste, wood, forestry waste and combinations thereof, and as further described below. Biomass has a carbohydrate content that comprises polysaccharides and oligosaccharides and may also comprise additional components, such as protein and/or lipid.

"Highly conserved" as used herein refers to the carbohydrate content of the lignocellulosic material after the processing steps described herein. In an embodiment of the invention, the highly conserved carbohydrate content provides for sugar yields after saccharification that are substantially similar to theoretical yields with minimal loss of sugar yield from the processes described herein. In an embodiment of the invention, highly conserved with reference to carbohydrate content refers to the conservation of greater than or equal to 85% of the biomass carbohydrate as compared to biomass prior to pretreating as described herein.

"Preprocessing" as used herein refers to processing of lignocellulosic biomass prior to pretreatment. Preprocessing is any treatment of biomass that prepares the biomass for pretreatment, such as mechanically milling and/or drying to the appropriate moisture contact.

"Biomass-solvent suspension" refers to a mixture of biomass and solvent. The biomass-solvent solution may comprise additional components such as alkylamines, thioglycolate, ammonia, sulfides, etc.

"Saccharification" refers to the production of fermentable sugars from primarily polysaccharides by the action of hydrolytic enzymes. Production of fermentable sugars from pretreated biomass occurs by enzymatic saccharification by the action of cellulolytic and hemicellulolytic enzymes.

"Pretreating biomass" or "biomass pretreatment" as used herein refers to subjecting native or preprocessed biomass to chemical or physical action, or any combination thereof, rendering the biomass more susceptible to enzymatic saccharification or other means of hydrolysis prior to saccharification. For example, the methods claimed herein may be referred to as pretreatment processes that contribute to rendering biomass more accessible to hydrolytic enzymes for saccharification.

"Pretreatment filtrate" means the free liquid that is in contact with the biomass following pretreatment and which is separated by filtration.

"Pretreated Biomass" as used herein refers to native or preprocessed biomass that has been subjected to chemical, physical or biological action, or any combination thereof, rendering the biomass more susceptible to enzymatic saccharification or other means of hydrolysis prior to saccharification.

"Air-drying the filtered biomass" can be performed by allowing the biomass to dry through equilibration with the air of the ambient atmosphere.

"Readily saccharifiable biomass" means biomass that is carbohydrate-enriched and made more amenable to hydrolysis by cellulolytic or hemi-cellulolytic enzymes for producing monomeric and oligomeric sugars, i.e., pretreated biomass as described herein.

"Carbohydrate-enriched" as used herein refers to the biomass produced by the process treatments described herein. In one embodiment the readily saccharifiable carbohydrate-enriched biomass produced by the processes described herein has a carbohydrate concentration of greater than or equal to 85% of the dried biomass by weight, while having removed 75% or greater of the starting biomass lignin content based on dry weight.

"Heating the biomass suspension" means subjecting the biomass suspended in a solvent to a temperature greater than ambient or room temperature. Temperatures relevant to the present pretreatments are from about 100 to about 220° C., or from about 140 to about 180° C., or any temperature within or approximately these ranges.

"Filtering free liquid under pressure" means removal of unbound liquid through filtration, with some pressure difference on opposite faces of the filter.

"Alkaline" or "under alkaline conditions" means a pH of greater than 7.0. In the present invention, "under alkaline conditions", also means a pH of the biomass-solvent suspension equal to or greater than the pKas of the nucleophiles present such that these are substantially deprotonated and more highly reactive than in their protonated states. These nucleophiles would include alkylamines, and ammonia, thiols, polysulfides and hydrosulfide (if present).

"Divalent alkane" means a linear, branched or cyclic alkane with two open valences.

"Alkylamine" means an alkane containing an —$NH_2$ group in place of one, two or three H atoms; e.g., monomethylamine, dimethylamine, trimethylamine, ethylamine, isopropyl-amine, ethylhexylamine, cyclohexylamine, and as further defined below.

"Air-dried sample" means a pretreated sample which has been allowed to air-dry at ambient temperature and pressure to the point where its moisture content is in equilibrium with that of the ambient air, typically ≧85% dry matter.

"Substantially lignin-free biomass" means a pretreated sample in which about ≧75% of the lignin is removed.

"Dry biomass" means biomass with a dry matter content of ≧85%. Methods for drying the biomass include exposure at ambient temperature to vacuum or flowing air at atmospheric pressure and or heating in an oven or a vacuum oven.

"Multi-component solvent" means a solvent containing organic solvent, water, and reagents capable of chemical attack on the lignin.

"Pressure vessel" is a sealed vessel that may be equipped or not with a mechanism for agitation of a biomass/solvent suspension, in which a positive pressure is developed upon heating the lignocellulosic biomass.

"Nucleophile" is a chemical reagent capable of forming a covalent bond with its reaction partner by contributing both of the bonding electrons.

"Hydrolysate" refers to the liquid in contact with the lignocellulose biomass which contains the products of hydrolytic reactions acting upon the biomass (either enzymatic or not), in this case monomeric and oligomeric sugars.

"Organosolv" means a mixture of organic solvent and water which is typically in contact with biomass and in which the lignin or its fragments are soluble.

"Enzyme consortium" or "saccharification enzyme consortium" is a collection of enzymes, usually secreted by a microorganism, which in the present case will typically contain one or more cellulases, xylanases, glycosidases, ligninases and esterases.

"Monomeric sugars" or "simple sugars" consist of a single pentose or hexose unit, e.g., glucose, xylose and arabinose.

"Delignification" is the act of removing lignin from lignocellulosic biomass. In the context of this application, delignification means fragmentation and extraction of lignin from the lignocellulosic biomass using an organic solvent under alkaline conditions at elevated temperatures in the presence of alkylamines and optionally various nucleophiles.

"Fragmentation" is a process in which lignocellulosic biomass is treated with organic solvent under alkaline conditions breaking the lignin down into smaller subunits.

"Selective extraction" is a process by which fragmented lignin is dissolved by treatment with an organic solvent under alkaline conditions leaving behind the polysaccharide.

"Simultaneous fragmentation and selective extraction" as used herein refers to a fragmentation reaction performed in organic solvent such that the lignin fragments go into solution as soon as they are released from the bulk biomass.

Methods for pretreating lignocellulosic biomass to produce readily saccharifiable biomass are provided. These methods provide economical processes for rendering components of the lignocellulosic biomass more accessible or more amenable to enzymatic saccharification. The pretreatment can be chemical, physical or biological, or any combination of the foregoing. In this disclosure the pretreatment is performed in the presence of nucleophiles, specifically in the presence of one or more alkylamine under alkaline conditions. Additional nucleophiles may also be present, such as $NH_3$, thiol, sulfide reagents, or combinations thereof. The presence of an organic solvent and alkaline conditions assists lignin fragmentation and removal and carbohydrate recovery.

In addition, the methods described in the present disclosure minimize the loss of carbohydrate during the pretreatment process and maximize the yield of solubilized (monomeric+oligomeric) sugars in saccharification.

As disclosed above the methods described herein include pretreating lignocellulosic material, with a solvent solution comprising the components described below, to produce a readily saccharifiable carbohydrate-enriched biomass.

Solvents

The methods described herein include use of an organic solvent for pretreating biomass and specifically for fragmentation and extraction of lignin. Solvents useful in the present methods are frequently referred to in the art as Organosolv (e.g., E. Muurinen (2000) Organosolv Pulping, A review and distillation study related to peroxyacid pulping Thesis, University of Oulu, pp. 314; S. Aziz, K. Sarkanen, Tappi J., 72/73: 169-175, 1989; A. K. Varsheny and D. Patel, J. Sci. Ind. Res., 47: 315-319, 1988; A. A. Shatalov and H. Pereira, BioResources 1:45-61, 2006; T. N. Kleinert, Tappi J., 57: 99-102, 1979; Practice of organosolv technology for biofuels, derived from Kleinert, which has advanced to the pilot scale using EtOH/$H_2O$ has been described (WO 20071051269), and X. Pan, N. Gilkes, J. Kadla, K. Pye, S. Saka, D. Gregg, K. Ehara, D. Xie, D. Lam, and J. Saddler, Biotechnol. Bioeng., 94: 851-861, 2006. While still at lab scale, use of acetone/$H_2O$ is described in U.S. Pat. No. 4,470,851. Further details on pretreatment technologies related to use of solvents and other pretreatments can be found in Wyman et al., (Bioresource Tech., 96: 1959, 2005); Wyman et al., (Bioresource Tech., 96: 2026, 2005); Hsu, ("Pretreatment of biomass" In Handbook on Bioethanol: Production and Utilization, Wyman, Taylor and Francis Eds., p. 179-212, 1996); and Mosier et al., (Bioresource Tech., 96: 673, 2005). Solvents are used herein for pretreating biomass to remove lignin. Delignification is typically conducted at temperatures of 165-225° C., at liquid to biomass ratios of 4:1 to 20:1, at liquid compositions of 50% organic solvent (v/v), and at reaction times between 0.5-12 h. A number of mono- and polyhydroxy-alcohols have been tested as solvents. Ethanol, butanol and phenol have been used in these reactions (Park, J. K., and Phillips, J. A., Chem. Eng. Comm., 65: 187-205, 1988).

The organosolv or organic solvent solution pretreatment in the present methods may comprise a mixture of water and an organic solvent at selected condition parameters that include temperature, time, pressure, solvent-to-water ratio and solids-to-liquid ratio. The solvent can comprise, but is not limited to, alcohols and aprotic solvents (solvents that do not have a hydrogen atom bound to an oxygen as in a hydroxyl group or a nitrogen as in an amine group or a sulfur as in a thiol group, e.g., ketones). The alcohols may include methanol, ethanol, propanol, butanol, pentanol and hexanol and isomers thereof and diols with the same number of carbon atoms, such as 1,2-ethanediol, 1,2-propandiol, 1,3-propanediol, 1,3-hexanediol.

The concentration of the solvent in solution (i.e. water) in the present invention is from about 2 to about 90% (v/v), or from about 10% to about 85% or from about 20% to about 80% or from about 30% to about 80% or more preferably from about 40% to about 70% (v/v). Specifically, for purposes of an embodiment of the methods herein, EtOH in $H_2O$ mixtures from about 0%-80% (v/v) ethanol concentrations were examined and solutions containing 40-70% (v/v) EtOH were found to be most effective.

Alkylamines

Alkylamines are used for pretreatment of biomass according to the present methods as components of the solvent solution. Alkylamines are low-cost materials and when used for pretreating biomass contribute to providing an overall economical process. Further, alkylamines may be recycled during pretreatment thereby increasing the efficiency and economy of the present methods.

Suitable alkylamines for this invention comprise: methylamine (MA), dimethylamine (DMA), trimethylamine (TMA), ethylamine, propylamine, and butylamine. The more suitable alkylamines for this invention include, but are not limited to MA and DMA. The concentration of the alkylamines according to the present method may be from about 1% to about 20 wt % of dry biomass.

The alkylamines employed herein have a combination of electron releasing, steric and H-bonding factors that influence the stability of the substituted ammonium cations in protic polar solvents, affecting the basic nature of amines (pKa), and affecting their activity as nucleophiles.

In accordance with the present methods it has been unexpectedly discovered that alkylamines, especially MA and DMA, are highly active in a concentration range of from 10 to 14% relative to dry weight of biomass. In this concentration range there is sufficient alkylamine to assure that the pH of the solvent solution remains high and that the concentration of alkylamine is sufficient to assure continued lignin fragmentation as pretreatment occurs.

During pretreatment of biomass as described herein, the alkylamines promote fragmentation of the lignin, the mechanism of which might include nucleophilic attack on the lignin aryl ether linkages, nucleophilic attack at the α-position of the quinone methides, formed under alkaline conditions, promoting the rupture of the β-aryl ether bond, or reduction of the quinone methide with elimination of the β-aryl ether. This fragmentation of the lignin into lower molecular weight components and the dissolution of these fragments in the organosolv solvent increases the exposure of the polysaccharide chains to cellulolytic and hemicellulolytic enzymes (such as cellulases and hemi-cellulases) for hydrolytic release of oligomeric and monomeric sugars.

Alkylamines are strong bases owing to electron donation to the amine nitrogen by the alkyl chain carbons, and consist of primary amines ($R—NH_2$), secondary amines (R—N—R') and tertiary amines where R is an alkyl chain. Specifically R could be selected from a group consisting of a monovalent, divalent or trivalent 1-6 carbon alkane, alkene or alkyne, linear, cyclic or branched. Examples of alkylamines include, mono, di- and tri-methylamine, mono, di- and tri-ethylamine, mono, di- and tri-propylamine, mono, di- and tri-butylamine. Alkylamines include mono-, di- and tri-amines, alcohol amines ($HO—R—NH_2$), diolamines (($HO)_2—R—NH_2$), alcohol diamines ($HO—R—(NH_2)_2$), thiolamines ($HS—R—NH_2$), dithiolamines (($HS)_2—R—NH_2$), thioldiamines ($HS—R—(NH_2)_2$) and alcohol thiolamines ($H_2N—R(OH)(SH)$) where R is as defined.

Alkylamines are also strong nucleophiles with pKas around 9-11. For example, the pKas of methylamine and dimethylamine (DMA) are 10.62 and 10.64, respectively. They were therefore chosen to study their effects on lignocellulosic biomass. Surprisingly, use of alkylamines in the present methods resulted in very substantial improved fragmentation and extraction of the lignin.

Further, carbohydrate and ultimately sugar recovery improved with use of the alkylamines which may function to protect the reducing ends of the polysaccharide chains by forming an imine (Schiff base), thereby decreasing sugar losses to "peeling" at alkaline pH and subsequent formation of furfural and hydroxymethyl furfural.

Further, an increase in polysaccharide recovery with increasing ethanol (solvent) concentration in the solvent solution was observed, which likely reflects a decreased hydrolysis of glucan and xylan during the pretreatment, accompanied by decreased solubility of xylose oligomers in the pretreatment filtrate. The increased lignin fragmentation and extraction with increasing ethanol concentration in the pretreatment solution comprising one or more alkylamine likely reflects an increase in the unprotonated form of the alkylamine and the increased solubility of the lignin fragments in the decreasingly polar solvent in the present methods.

Additional Components of the Solvent Solution

According to the present method, the solvent solution comprising one or more alkylamine may optionally comprise additional components. The additional components may include other nucleophiles such as at least one additional (inorganic) base, such as sodium hydroxide, ammonia, sodium carbonate, potassium hydroxide, potassium carbonate, calcium hydroxide and calcium carbonate.

The one or more additional base may be added in an amount that is combined with alkylamine to form an amount of total base that is less than about 20 wt % relative to biomass dry weight. Preferably, the total one additional base plus alkylamine is in an amount that is less than about 16%, or about 0%, 2%, 4%, 6%, 8%, 10%, 12%, 14% or 16% relative to dry weight of biomass. The one or more additional base may be used at various concentrations of at least from 0.5% to about 16%. More suitable are the concentrations from 1% to 10%. Most suitable are the concentrations between 2% to 8%.

In an embodiment, NaOH may be employed as an additional component of the solvent solution in the presence of alkylamines resulting in increasing lignin fragmentation and extraction, and resulting in an increased accessibility of the carbohydrate-enriched biomass to enzymatic saccharification. NaOH may be used specifically in an EtOH in $H_2O$ solvent solution. Use of NaOH may include the addition of a catalyst, such as anthraquinone, to the solvent solution for further lignin fragmentation.

In another embodiment, ammonia may be employed as an additional component of the solvent solution in the presence of alkylamines, resulting in increasing lignin fragmentation and extraction, and resulting in an increased accessibility of the carbohydrate-enriched biomass to enzymatic saccharification. A further specific embodiment is the use of ammonia and methylamine in the solvent solution. One aspect includes use of elemental sulfur and ammonia in solvent solutions comprising methylamine as the alkylamine in the solvent solution. For example, such a solvent solution may comprise 20-80% v/v EtOH in $H_2O$ with 1% elemental sulfur, 2% to 16% $NH_3$ (w/w biomass) and methylamine.

High glucose and xylose saccharification yields were observed from lignocellulosic biomass following pretreatment in solvent solutions comprising 70% EtOH in $H_2O$ (v/v) and 1% elemental sulfur and 14% methylamine (both w/w biomass). However, pretreatments with increasing replacement of methylamine with ammonia in 70% EtOH in $H_2O$, in the presence of 1% elemental sulfur (w/w biomass), resulted in a lowering of the amount of monomeric sugar released upon subsequent enzymatic saccharification (Example 11).

In another embodiment, thioglycolate is added to the solvent solution in the presence of alkylamines resulting in increased lignin fragmentation and extraction, and accordingly, increased accessibility of the readily saccharifiable biomass to enzymatic saccharification. In the present invention, concentrations of thioglycolate from 0.5 to 15% may be used. More specifically concentrations of 1 to 3% are more useful. Even more specifically concentrations of ~2% would be most useful for the present invention.

In another embodiment ammonium sulfide is added to the solvent solution in the presence of alkylamines resulting in increasing lignin fragmentation and extraction, and resulting in an increased accessibility of the carbohydrate-enriched biomass to enzymatic saccharification. Sulfide is a good nucleophile and reductant. In addition, the sulfide may potentially be generated in the alkaline organic solvent solution pretreatment solution by sparging with $H_2S$ or by disproportionation of elemental sulfur. In the present invention, concentrations of ammonium sulfide from 0.5% to 15% could be used. More specifically concentrations of 1% to 6% are more useful. Even more specifically concentrations of 2% to 4% would be most useful for the present invention.

In another embodiment, as mentioned above, elemental sulfur is added to the solvent solution in the presence of alkylamines resulting in solubilization and disproportionation of the sulfur to produce polysulfide, sulfide and hydrosulfide. As in the case of ammonium sulfide, this addition is beneficial to pretreatment, increasing lignin fragmentation and extraction and resulting in an increased accessibility of the readily saccharifiable biomass to enzymatic saccharification. In the present invention, concentrations of elemental sulfur from 0.05% to 5% (w/w biomass) could be used. More specifically concentrations of 0.5 to 2% (w/w biomass) are more useful. Even more specifically concentrations of ~1% (w/w biomass) would be most useful for the present invention.

Lignocellulosic Biomass

The lignocellulosic biomass pretreated herein includes, but is not limited to, bioenergy crops, agricultural residues, municipal solid waste, industrial solid waste, sludge from paper manufacture, yard waste, wood and forestry waste. Examples of biomass include, but are not limited to corn cobs, crop residues such as corn husks, corn stover, grasses, wheat, wheat straw, barley, barley straw, hay, rice straw, switchgrass, waste paper, sugar cane bagasse, sugar cane straw, yellow poplar, sorghum, soy, components obtained from milling of grains, trees, branches, roots, leaves, wood chips, sawdust, shrubs and bushes, vegetables, fruits, flowers and animal manure.

In one embodiment, the lignocellulosic biomass includes agricultural residues such as corn stover, wheat straw, barley straw, oat straw, rice straw, canola straw, and soybean stover; grasses such as switchgrass, miscanthus, cord grass, and reed canary grass; fiber process residues such as corn fiber, beet pulp, pulp mill fines and rejects and sugar cane bagasse; sugar cane straw and sorghum; forestry wastes such as yellow poplar, aspen wood, other hardwoods, softwood and sawdust; and post-consumer waste paper products; as well as other crops or sufficiently abundant lignocellulosic material.

In another embodiment, biomass that is useful for the invention has a relatively high carbohydrate content, is relatively dense, and/or is relatively easy to collect, transport, store and/or handle.

In another embodiment of the invention, biomass that is useful includes corn cobs, corn stover, sugar cane bagasse, sugar cane straw, yellow poplar and switchgrass.

The lignocellulosic biomass may be derived from a single source, or can comprise a mixture derived from more than one source; for example, biomass could comprise a mixture of corn cobs and corn stover, or a mixture of stems or stalks and leaves.

In the present method, the biomass dry weight is at an initial concentration of at least about 9% up to about 80% of the weight of the biomass-solvent suspension during pretreatment. More suitably, the dry weight of biomass is at a concentration of from about 15% to about 70%, 15% to about 60%, or about 15% to about 50% of the weight of the biomass-solvent suspension. The percent of biomass in the biomass-solvent suspension is kept high to reduce the total volume of pretreatment material, decreasing the amount of solvent and reagents required and making the process more economical.

The biomass may be used directly as obtained from the source, or may be subjected to some preprocessing, for example, energy may be applied to the biomass to reduce the size, increase the exposed surface area, and/or increase the accessibility of lignin and of cellulose, hemicellulose, and/or oligosaccharides present in the biomass to organosolv pretreatment and to saccharification enzymes used, respectively, in the second and third steps of the method. Energy means useful for reducing the size, increasing the exposed surface area, and/or increasing the accessibility of the lignin, and the cellulose, hemicellulose, and/or oligosaccharides present in the biomass to the organosolv pretreatment and to saccharification enzymes include, but are not limited to, milling, crushing, grinding, shredding, chopping, disc refining, ultrasound, and microwave. This application of energy may occur before or during pretreatment, before or during saccharification, or any combination thereof.

Drying prior to pretreatment may occur as well by conventional means, such as exposure at ambient temperature to vacuum or flowing air at atmospheric pressure and or heating in an oven at atmospheric pressure or a vacuum oven.

Pretreatment Conditions

Pretreatment of biomass with the solvent solution comprising one or more alkylamine is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (Jaygo Manufacturing, Inc., Mahwah, N.J.), and a steam gun reactor (described in General Methods Autoclave Engineers, Erie, Pa.). Much larger scale reactors with similar capabilities may be used. Alternatively, the biomass and organosolv solution may be combined in one vessel, then transferred to another reactor. Also biomass may be pretreated in one vessel, then further processed in another reactor such as a steam gun reactor (described in General Methods; Autoclave Engineers, Erie, Pa.).

The pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-organosolv mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, NY). The pretreatment reaction may be carried out either as a batch or a continuous process.

Prior to contacting the biomass with solvent, vacuum may be applied to the vessel containing the biomass. By evacuating air from the pores of the biomass, better penetration of the solvent into the biomass may be achieved. The time period for applying vacuum and the amount of negative pressure that is applied to the biomass will depend on the type of biomass and can be determined empirically so as to achieve optimal pretreatment of the biomass (as measured by the production of fermentable sugars following saccharification).

The heating of the biomass with solvent is carried out at a temperature of from about 100° C. to about 220° C., about 150° C. to 200° C., or about 165° C. to about 195° C. The heated solution may be cooled rapidly to room temperature. In still another embodiment, the heating of the biomass is carried out at a temperature of about 180° C. Heating of the biomass-solvent suspension may occur for about 5 minutes to about 5 hours, or for about 30 minutes to about 3 hours, or more preferably from about 1 to 2 hours.

The pretreatment of biomass with the solvent solution and one or more alkylamine occurs under alkaline conditions at a pH that is equal to or greater than the pKa of the nucleophiles present. Deprotonation typically increases the reactivity of the nucleophile. The nucleophiles present, in addition to alkylamine, can include ammonia, thiols, polysulfides, or hydrosulfide.

For the pretreatment methods described herein, the temperature, pH, time of pretreatment and concentration of reactants such as the organic solvent and alkylamine solutions and the concentration of one or more additional reagents, biomass concentration, biomass type and biomass particle size are related; thus these variables may be adjusted as necessary for each type of biomass to optimize the pretreatment processes described herein.

Following pretreatment at elevated temperature, the biomass is filtered under pressure. The filtration may either be preceded or not by cooling. Following filtration, the biomass may be washed one or more times with hydrated organic solvent at elevated or at ambient temperature. It may then either be washed with water or dried to remove the organic solvent and then saccharified. Methods for drying the biomass include exposure at ambient temperature to vacuum or flowing air at atmospheric pressure and or heating in an oven at atmospheric pressure or in a vacuum oven as described more fully herein.

To assess performance of the pretreatment, i.e., the production of readily saccharifiable carbohydrate-enriched biomass and subsequent saccharification, separately or together, the theoretical yield of sugars derivable from the starting biomass can be determined and compared to measured yields. Pretreatment performance may be further assessed by relating how enzyme loadings affect target product yields in overall system performance.

Further Processing
Saccharification

Following pretreatment, the readily saccharifiable carbohydrate-enriched biomass comprises a mixture of organic solvent, the one or more alkylamine and any additional components of the solvent solution such as thioglycolate or ammonia; fragmented and extracted lignin; and polysaccharides. Prior to further processing, the one or more alkylamine and/or additional solvent components such as thioglycolate or ammonia and lignin fragments may be removed from the pretreated biomass by filtration and washing the sample with EtOH in $H_2O$ (0% to 100% EtOH v/v) or water. The biomass may be washed with water to remove EtOH or dried resulting in carbohydrate-enriched, readily saccharifiable biomass and the concentration of glucan, xylan and acid-insoluble lignin content of said biomass may be determined using analytical means well known in the art. It is a real benefit of this invention that the pretreated biomass can be either washed with water or dried for saccharification. The readily saccharifiable biomass may then be further hydrolyzed in the presence of a saccharification enzyme consortium to release oligosaccharides and/or monosaccharides in a hydrolysate.

Surfactants such as Tween 20 or Tween 80 or polyoxyethylenes such as PEG 2000, 4000 or 8000 may be added to improve the saccharification process (U.S. Pat. No. 7,354,743 B2, incorporated herein by reference). The addition of surfactant (e.g., Tween 20) to the enzymatic saccharification often enhances the rate and yield of monomeric sugar release. It is likely that the surfactant coats any residual lignin, decreasing the non-productive binding of the enzyme to the lignin. An alternative approach is to either enhance the extraction of lignin in the pretreatment or to modify the lignin chemically such that less enzyme is lost to lignin adsorption.

Saccharification enzymes and methods for biomass treatment are reviewed in Lynd, L. R., et al., (Microbiol. Mol. Biol. Rev., 66: 506-577, 2002). The saccharification enzyme consortium may comprise one or more glycosidases; the glycosidases may be selected from the group consisting of cellulose-hydrolyzing glycosidases, hemicellulose-hydrolyzing glycosidases, and starch-hydrolyzing glycosidases. Other enzymes in the saccharification enzyme consortium may include peptidases, lipases, ligninases and esterases.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223: 1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650, 1999, respectively]) of the general group "hydrolases" (EC 3). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, in isolated form, such as Spezyme® CP cellulase (Genencor International, Rochester, N.Y.) and Multifect® xylanase (Genencor). In addition, saccharification enzymes may be expressed in host microorganisms at the biofuels plant, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. and most typically 45-50° C. The pH optimum can range from about 2 to about 11. In another embodiment, the pH optimum used with the saccharification enzyme consortium in the present method ranges from about 4 to about 5.5.

The saccharification can be performed for a time of about several minutes to about 120 hours, and preferably from about several minutes to about 48 hours. The time for the reaction will depend on enzyme concentration and specific activity, as well as the substrate used, its concentration (i.e., solids loading) and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using cellulases stable and more active at higher pHs and temperatures followed by hemicellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem., 31: 426-428, 1959). Alternatively, sugars can be measured by HPLC using an appropriate column as described below.

Fermentation to Target Products

The readily saccharifiable biomass produced by the present methods may be hydrolyzed by enzymes as described above to produce fermentable sugars which then can be fermented into a target product. "Fermentation" refers to any fermentation process or any process comprising a fermentation step. Target products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, 1,2-ethanediol, furfural, polyhydroxyalkanoates, cis,cis-muconic acid, and animal feed (Lynd, L. R., Wyman, C. E., and Gerngross, T. U., Biocom. Eng., Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproduction of products may also be produced, such as multiple organic products from fermentable carbohydrate. Lignin-rich residues remaining after pretreatment and fermentation can be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., supra). SSCF includes the cofermentation of multiple sugars (Sheehan, J., and Himmel, M., Biotechnol. Prog. 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Rev., 66: 506-577, 2002).

These processes may be used to produce target products from the readily saccharifiable biomass produced by the pretreatment methods described herein.

Advantages of the Present Methods

Methods described in this invention for pretreatment of the lignocellulosic biomass using fragmentation and selective extraction of lignin at elevated temperatures under alkaline conditions in combination with one or more alkylamine and various nucleophiles provide a cost-effective process to obtain carbohydrate-enriched biomass for enzymatic saccharification. Such biomass then, produces very high yields of fermentable sugars (glucose, as well as xylose) for their bioconversion to value-added chemicals and fuels.

Among the key weaknesses of current organosolv processes described in the literature are: the poor recoveries of carbohydrate, particularly xylose, following pretreatment, the requirement for separate hexose and pentose streams, the production of sugar breakdown products, the use of large amounts of solvent and high capital cost. For example, certain existing processes include use of acidic organosolv conditions and produce hydrolysates of hemicellulose and cellulose. The greater lability of the hemicellulose under acidic conditions results in the formation of breakdown products of monomeric xylose (e.g., furfural), greatly reducing the recovery of xylose (Pan et al., supra). In one version of this process (Arato, C., Pye, E. K., and Gjennestad, G., Appl. Biochem. Biotech. 121-124: 871-882, 2005), the hemicellulose is hydrolyzed under acidic conditions and the cellulose, following neutralization, is hydrolyzed enzymatically. The need to neutralize the acid prior to saccharification, the partial loss of xylose, and the processing of separate pentose and hexose streams all add to the costs of the process. Furthermore, the use of acidic conditions, requires the use of alloys in the reactors and piping that substantially add to the capital cost of the equipment.

This disclosure describes development of a highly selective process in which the lignin is selectively fragmented and extracted using inexpensive reagents and the hemicellulose and the cellulose remain together in the biomass to be later saccharified enzymatically. The amount of lignin extracted into the organic solvent solution is ≧75% and the xylan and glucan recoveries in the residual biomass are close to quantitative. The high recoveries of polysaccharide arise because of the use of alkaline conditions that diminish hemicellulose hydrolysis and sugar breakdown, the use of ammonia or alkylamines that prevent polysaccharide peeling under alkaline conditions and the high ethanol content of the organic solvent solution which limits carbohydrate hydrolysis and which renders insoluble xylose oligomers. In addition, the alkaline conditions used do not require the use of exotic alloys in the equipment, thereby lowering capital cost. Performing this process with little or no inorganic salt among the reactants or products (e.g., NaOH, $Na_2CO_3$, $CaSO_4$) results in little or no cost associated with disposal of inorganic waste material at the end. The unreacted reagents (e.g., EtOH, alkylamine and $HS^-/S^=$) are recyclable, with, in the case of EtOH and alkylamine, low boiling points and low heats of vaporization relative to water, thereby lowering energy requirements and operating cost. Many of the processes described in the literature use large solvent to biomass ratios. In the present case, the use of alkaline conditions and the substantial fragmentation of the lignin by the added nucleophiles means that the solvent streams can accumulate high concentrations of lignin, reducing the need for large solvent volumes and at the same time reducing the loss of trace amounts of solubilized carbohydrate. Finally, the residual carbohydrate saccharifies well using enzymes, likely because of the high level of extraction of lignin fragments in the pretreatment, the effective scission of ester linkages between hemicellulose and lignin, and some lowering of the degree of polymerization of the polysaccharide. The use of organic solvent improves the wettability of the biomass and the ability to easily penetrate into the pores of the substrate. The combination of the alkaline conditions using a high pKa organic base (e.g., alkylamine) and the presence of strong nucleophiles (e.g., alkylamines, sulfide) enables this process to produce readily saccharifiable biomass, even for those feedstocks with high lignin content (e.g., switchgrass, bagasse). The universality of the pretreatment is demonstrated in Examples 12 and 14, where a broad range of lignocellulosic materials, represented here by corn cob, switch grass, sugar cane bagasse, sugar cane straw and yellow poplar are shown to saccharify well following pretreatment.

EXAMPLES

Pretreatment of Biomass to Obtain Readily Saccharifiable Carbohydrate-Enriched Biomass The goal of the experimental work described below was to develop an economical pretreatment process for lignocellulose that maximized both lignin extraction and sugar retention and to, produce a readily saccharifiable carbohydrate-enriched biomass that, upon enzymatic saccharification, would give maximal monomeric sugar yields. The approach adopted was to selectively fragment and extract the lignin into a suitable solvent while retaining the sugars in the solids residue. It was found that the combined presence of an organic solvent and alkylamines and optionally certain nucleophiles like $NH_3$, thiol, polysulfide and sulfide selectively fragmented and dissolved the lignin components of the biomass leaving behind readily-saccharifiable carbohydrate-enriched biomass.

Switchgrass, corn cob, sugar cane straw, yellow poplar and sugar cane bagasse were milled in a Wiley knife mill through a 1 mm screen prior to pretreatment.

The following abbreviations are used in the Examples: "HPLC" is High Performance Liquid Chromatography, "C" is degrees Centigrade or Celsius; "%" is percent; "wt" is weight; "w/w" is weight for weight; "mL" is milliliter; "OD" is outer diameter; "ID" is internal diameter; "h" is hour(s); "rpm" is revolution per minute; "EtOH" is ethanol; "mg/g" is milligram per gram; "g/100 mL" is gram per 100 milliliters; "N" is normal; "g" is gram; "NaOH" is sodium hydroxide; "w/v" is weight per volume; "v/v" is volume for volume; "$NH_3$" is ammonia; "mm" is millimeter; "mL/min" is milliliter per minute; "min" is minutes; "mM" is millimolar.

Materials

Sulfuric acid, ammonium hydroxide, acetic acid, acetamide, yeast extract, 2-morpholinoethanesulfonic acid (MES), potassium phosphate, glucose, xylose, tryptone, sodium chloride and citric acid, monomethyl and dimethylamine were obtained from Sigma-Aldrich (St. Louis, Mo.). Spezyme CP and Multifect CX12L were from Genecor (Genencor International, Palo Alto, Calif.) and Novozyme 188 was from Novozyme (Novozymes, 2880 Bagsvaerd, Denmark).

Example 1

Effective Ethanol Concentration

The purpose of this Example was to examine the effect of the concentration of solvent (e.g., ethanol) in water on the recovery of carbohydrate and on the solubilization/extraction of lignin in the absence of pH control. Bagasse (0.2 g, 95.78% dry matter) was suspended in 1.56 mL of an EtOH/water solution containing various concentrations (from 0 to 80%) of EtOH. The suspensions were loaded into type 316 stainless steel tubing (¼ inches ID, ⅜ inches OD, 4 inches long) capped by Swagelock fittings (Penn Fluid System Technologies, Huntingdon Valley, Pa.). These were placed in a fluidized sand bath (Techne Model SBS-4, Techne Inc., Burlington, N.J.) and heated at 180° C. for 2 h and cooled rapidly by plunging into a water bath at room temperature. The samples were removed from the tubes and filtered by centrifugation at 14,000 rpm using Spin-X filters (Costar, Corning Inc., Corning N.Y.) at room temperature in a table top centrifuge (Spectrifuge 16M, Labnet International Inc., Edison, N.J.) to remove the dissolved lignin. The retentate of each sample was washed (4×) with 0.5 mL of EtOH/$H_2O$ using the same EtOH concentration as used in the 180° C. treatment (0-80% EtOH in $H_2O$). The samples were then allowed to air dry at room temperature (to ~92% dry matter) and the glucan, xylan and acid-insoluble lignin contents of the residues determined using the National Renewable Energy Laboratory (NREL) procedure (Determination of Structural Carbohydrates and Lignin in Biomass—Version 2006, Amie Sluiter et al., available from the NREL website).

Subsequent Enzymatic Saccharification

The air-dried sample prepared above was suspended in 50 mM citrate buffer, pH 4.6 at a ~14% solids loading. The saccharification enzymes, e.g. Spezyme CP, Multifect CX12L and Novozyme 188 were added at concentrations of 6:3:6 mg/g cellulose, respectively. Also added were 1% (w/v) Tween 20 and 0.01% (w/v) $NaN_3$, the latter to prevent microbial growth. Samples (~0.4 mL) were placed in screw cap vials containing two 5 mm glass beads and incubated at 46° C. on a rotary shaker run at 250 rpm. Aliquots were removed for analysis at 4 h and at every 24 h interval from the start and diluted 41.25-fold with 0.01 N $H_2SO_4$. The samples were then filtered through Spin-X filters and the filtrates were analyzed by HPLC (Agilent series 1100/1200, Agilent Technologies, Wilmington, Del.). A BioRad HPX-87H Aminex column (Bio-Rad Laboratories, Hercules Calif. 94547 was used to fractionate the released sugars using 0.01 N $H_2SO_4$ as the mobile phase at a flow rate of 0.6 mL/min. The column was maintained at 60° C. A differential refractive index detector was used to detect the eluted sugars and was maintained at 55° C. The retention times for glucose, xylose and arabinose were 9.05, 9.72 and 10.63 min, respectively. Table 1A outlines the percentages of glucan and xylan recovery and the percent change in acid insoluble (AI) lignin content after pretreatments at EtOH concentrations of 0%-80%.

TABLE 1A

Glucan and xylan recovery following pretreatment according to Example 1

| Pretreatment (% EtOH in water) | % Glucan recovery in residue | % Xylan recovery in residue | AI lignin content % change |
|---|---|---|---|
| 0 | 83.0% | 29.0% | +27.6% |
| 20 | 88.7% | 30.8% | +15.2% |
| 40 | 86.0% | 57.6% | −10% |
| 60 | 91.9% | 87.4% | −25.6% |
| 80 | 88.6% | 91.1% | −28.8% |

Results shown in Table 1A indicate that lignin extraction increased with increasing EtOH content presumably because the solubility of lignin increased with increasing EtOH concentration. However, the amount of lignin extracted remained modest even at high ethanol concentrations.

Hemicellulose hydrolysis and the solubility of xylose oligomers decreases with increasing EtOH, increasing the recovery of xylan and xylose oligomers in the residue. The amount of acetate liberated by the pretreatment also decreased with increasing EtOH content, consistent with decreasing auto hydrolysis of the biomass at increasing EtOH concentration.

Table 1B shows the glucose and xylose yields after 96 h of enzymatic saccharification following pretreatment at different EtOH concentrations. The saccharification of cellulose increased when the concentration of EtOH in pretreatment was increased from 0 to 20%, but then declined with higher pretreatment concentrations of EtOH. A likely decrease in partial hydrolysis of lignin and cellulose (increase in degree of polymerization, of cellulose which lowered the glucose yield on subsequent saccharification—Table 1B) was observed at concentrations of more than 20% EtOH.

TABLE 1B

Monomeric glucose and xylose yields following enzymatic saccharification for 96 h, pretreated as described in Example 1

| % EtOH in water (v/v) | Glucose monomer saccharification only (% theoretical yield) | Xylose monomer saccharification only (% theoretical yield) | Glucose monomer overall yield (% theoretical yield) | Xylose monomer overall yield (% theoretical yield) |
|---|---|---|---|---|
| 0 | 38.43 | 34.98 | 31.86 | 10.16 |
| 20 | 44.48 | 45.52 | 39.46 | 14.01 |
| 40 | 29.62 | 38.55 | 25.45 | 22.23 |
| 60 | 16.81 | 24.64 | 15.45 | 21.52 |
| 80 | 6.8 | 7.22 | 6.02 | 7.01 |

The monomeric sugar recoveries (Table 1B), particularly of xylose, were quite poor at the lower EtOH concentrations. At low EtOH concentration, the acidic conditions, produced at high temperatures by hydrolysis of the acetyl groups of the hemicellulose, hydrolyze the hemicellulose. The solubilized xylose and some glucose is lost in the filtration and washes that follow the pretreatment. At higher EtOH concentrations there is less partial hydrolysis of the cellulose, hemicellulose and lignin which lowers the saccharification yield. The behavior at the low and high ethanol concentrations together produce low overall yields of monomeric glucose and xylose.

Example 2

Effect of Alkaline Organic Solvent Solution Pretreatment on Lignin Extraction

The purpose of this Example was to examine the effect of raising the pH on organic solvent solution pretreatment at different $EtOH/H_2O$ ratios on carbohydrate retention and lignin extraction and on monomeric sugar during subsequent enzymatic saccharification. Given that autohydrolysis lowers the pH, hydrolyzes xylan, and promotes the loss of xylose, the pH of the pretreatment was elevated by the addition of NaOH. The effect of higher pH on xylose recovery is demonstrated below. Sugar cane bagasse (0.25 g, 95.78% dry matter) was suspended in 1.75 mL of a solvent containing EtOH (20-80% in water) and 8% NaOH (w/w biomass) plus 1 mg anthraquinone (AQ, a catalyst for lignin fragmentation). The initial pH of this solution was ~13.7. As described in Example 1, the suspensions were loaded into type 316 stainless steel tubing, capped, treated at 168° C. for 140 min and cooled in room-temperature water. The samples were removed from the pressure vessels, filtered, washed, air-dried and analyzed all as described above in Example 1. The glucan, xylan, arabinan contents and change in lignin content following pretreatment are shown in Table 2A.

Subsequent enzymatic saccharification was carried out as described in Example 1 except that the Spezyme:Multifect:Novozymes 188 ratio was 12:6:1.2 mg/g dry solids in the presence of 1% Tween 20 (w/v). Table 2B shows the monomeric sugar yields after 96 h of enzymatic saccharification of biomass previously pretreated at the different EtOH concentrations.

TABLE 2A

Glucan, xylan and arabinan yields following pretreatment according to Example 2

| Pretreatment % EtOH in water | % Glucan recovery in residue | % Xylan recovery in residue | % Arabinan recovery in residue | Al lignin content % change |
|---|---|---|---|---|
| 20 | 77.5% | 74.6% | 51.3% | −48 |
| 45 | 84.0% | 85.1% | 68.0% | −64 |
| 60 | 83.6% | 85.5% | 76.0% | −63 |
| 70 | 81.3% | 84.2% | 75.8% | −65 |
| 80 | 80.0% | 84.2% | 86.6% | −50 |

TABLE 2B

Monomeric glucose and xylose yields following enzymatic saccharification for 96 h, pretreated as described in Example 2

| % EtOH in H$_2$O | Glucose monomer saccharification only (% theoretical yield) | Xylan monomer saccharification only (% theoretical yield) | Glucose monomer overall yield (% theoretical yield) | Xylose monomer overall yield (% theoretical yield) |
|---|---|---|---|---|
| 20 | 57.72 | 68.56 | 44.7 | 51.2 |
| 45 | 58.19 | 73.08 | 48.9 | 62.2 |
| 60 | 49.51 | 64.56 | 41.4 | 55.2 |
| 70 | 24.48 | 39.06 | 19.9 | 32.9 |
| 80 | 0.63 | 1.33 | 0.5 | 1.1 |

As can be seen in Tables 2A and 2B, the alkaline conditions of this experiment substantially increased the retention of xylan in the pretreatment compared to the autohydrolysis experiments of Example 1. This effect was most pronounced at low EtOH concentrations. The NaOH prevented the solution from becoming acidic (final pH~10.7) and therefore protected the hemicellulose from acid-catalyzed hydrolysis. In addition, significantly more lignin was extracted, presumably through base catalyzed fractionation of the lignin. The overall monomeric sugar yields following saccharification were substantially higher than those observed in Example 1. The higher sugar recovery and the greater lignin extraction in the pretreatment, increased the yields of the subsequent enzymatic saccharification. The xylose and glucose saccharification yields peaked at ~45% EtOH as a consequence of two opposing processes, i.e., the increasing extraction of lignin at higher EtOH which tends to increase the sugar yields, and the decreasing partial hydrolysis of hemicellulose and of lignin as the EtOH concentration is further increased. It is likely that the formation of quinone methides, which could repolymerize or react with sugars, and "peeling' and alkaline scission reactions of polysaccharide all together contribute to limit the overall sugar yields.

Example 3

The Effect of Alkylamines on Pretreatment of Biomass Prior to Saccharification

The purpose of this Example was to study the effect of the presence of alkylamines in the organic solvent solution (70% EtOH in water v/v) on the lignin content of the biomass following pretreatment and on the carbohydrate recovery following pretreatment and saccharification.

Sugar cane bagasse (0.375 g, 95.78% dry matter) was suspended in 1.125 mL of solvent containing 70% EtOH in H$_2$O (v/v). In addition, the solvent contained variable amounts (6, 10 or 14%) of dimethylamine (DMA, w/w biomass). The initial pHs of these solvents were 12.50, 12.68 and 12.80, respectively. pH was adjusted using NaOH. The suspensions were loaded into type 316 stainless steel pressure vessels (3/16 inches ID, ¼ inches OD, 4 inches long), capped and treated as described above in Example 1, except that solids loading was higher and the samples were heated at 168° C., for 140 min. The results of the pretreatment are summarized in Table 3A.

TABLE 3A

Glucan, xylan and arabinan yields following Bagasse L/S = 3.1 (v/w) pretreatment

| Sample 70% EtOH (w/v) plus (w/w biomass) | % Glucan recovery in solids | % Xylan recovery in solids | % Arabinan recovery in solids | Al lignin % change in content | Initial pH |
|---|---|---|---|---|---|
| 6% DMA | 95.6% | 103.5% | 86.0% | −43% | 12.50 |
| 10% DMA | 98.5% | 106.4% | 90.0% | −48% | 12.68 |
| 14% DMA | 92.3% | 97.1% | 95% | −53% | 12.80 |

As can be seen in Table 3A the extraction of lignin increased with increasing concentration of DMA, consistent with an enhanced fragmentation of the lignin at higher amine concentrations. In contrast with Example 2, the carbohydrate recovery following pretreatment with DMA in 70% EtOH is considerably higher. It is likely that losses of carbohydrate due to "peeling" reactions at alkaline pH are prevented or limited by the use of DMA, either because the pH is not quite as high with 8% NaOH or because DMA or some breakdown to MMA and NH$_3$ blocks the "peeling" reactions through the formation of imines at the reducing end of the polysaccharide.

Enzymatic saccharification following pretreatment was carried out as described in Example 1 except that the Spezyme:Multifect:Novozymes 188 ratio was 6.68:3.34:1.67 mg/g dry solids in the presence of 1% Tween 20 (w/v). The solids loading was 14 wt %. The monomeric saccharification yields are shown in Table 3B.

TABLE 3B

Monomeric glucose and xylose yields following enzymatic saccharification for 96 h

| Sample 70% EtOH (w/v) plus (w/w biomass) | Glucose monomer saccharification only (% theoretical yield) | Xylose monomer saccharification only (% theoretical yield) | Glucose monomer overall (% theoretical yield) | Xylose monomer overall (% theoretical yield) |
|---|---|---|---|---|
| 6% DMA | 70.44 | 63.45 | 67.34 | 65.67 |
| 10% DMA | 73.04 | 67.44 | 71.94 | 71.75 |
| 14% DMA | 73.28 | 72 | 67.64 | 69.91 |

Table 3B shows that the monomeric sugar yields upon enzymatic saccharification following pretreatment with DMA were surprisingly far higher than those following pretreatment with 8% NaOH in 70% EtOH. In addition, the monomeric sugar yields increased with DMA concentration in the pretreatment solvent.

Example 4

Dimethylamine Produced the Highest Yield Upon Enzymatic Saccharification

The purpose of this Example was to compare the carbohydrate yields following pretreatment and enzymatic saccharification as a function of the content of the pretreatment solution, comparing DMA with $NH_3$ alone or $NH_3$ plus NaOH. An experiment was performed in which the pretreatment was performed as outlined in Example 3 except that the 70% $EtOH/H_2O$ (v/v) solvent (1.125 mL), in which the bagasse (0.375 g) was suspended, contained either 8% $NH_3$, 6% $NH_3$ plus 2% NaOH or 14% DMA (all w/w biomass) and the experiment was performed for 140 min at 168° C. The pretreatment recoveries of glucan, xylan and arabinan and the extraction of lignin are tabulated in Table 4A.

Enzymatic saccharification was carried out as described in Example 3. The saccharification yields in the absence of Tween 20 at 96 h following pretreatment in 70% EtOH plus different additives (w/w biomass) are shown in Table 4B.

TABLE 4A

Yields of glucan, xylan, and arabinan following pretreatment

| Sample 70% EtOH in $H_2O$ (w/v) plus additives (w/w biomass) | % Glucan recovery in solids | % Xylan recovery in solids | % Arabinan recovery in solids | Al lignin content % change | Initial pH |
|---|---|---|---|---|---|
| 14% DMA | 92.3% | 97.1% | 95% | −53% | 12.80 |
| 6% $NH_3$ + 2% NaOH | 97.8 | 107 | 92.4 | −47% | 14.0 |
| 8% $NH_3$ | 92.0% | 100% | 84.0% | −20% | 12.12 |

TABLE 4B

Monomeric glucose and xylose yields following enzymatic saccharification for 96 h

| Sample 70% EtOH in $H_2O$ (w/v) plus additives (w/w biomass) | Glucose monomer saccharification only (% theoretical yield) | Xylose monomer saccharification only (% theoretical yield) | Glucose monomer overall (% theoretical yield) | Xylose monomer overall (% theoretical yield) |
|---|---|---|---|---|
| 14% DMA | 63.54 | 63.43 | 58.65 | 61.59 |
| 6% $NH_3$ + 2% NaOH | 52.38 | 45.7 | 51.23 | 48.89 |
| 8% $NH_3$ | 39.66 | 36.94 | 36.49 | 36.94 |

Of the three conditions used, DMA pretreatment produced the greatest degree of fragmentation and extraction of lignin, giving the greatest enzyme accessibility to cellulose and hemicellulose and producing the highest monomeric sugar yields.

Example 5

Comparison of Methylamine and Dimethylamine for Pretreatment of Biomass

In this Example, pretreatment was performed as in Example 3 except that the sugar cane bagasse was suspended in 70% EtOH in $H_2O$ (v/v) containing either methylamine (MA) or dimethylamine (DMA). The pretreatments were performed at 168° C. for 140 min for those samples containing 6, 10 and 14% DMA (w/w biomass) and at 187° C. for 1 h for those samples containing 6, 10 and 14% MA and 14% DMA (w/w biomass) as shown in Table 5A. While the two sets of experiments (MA and DMA) were performed at two different temperatures and times, the temperature and time have little impact on the pretreatment recovery and the saccharification yields for each of the alkylamines (for pretreatments between 168° C. for 140 min and 187° C. for 1 h) and are within the noise of the measurement (see for example 14% DMA at 168° C. and 187° C.). There does not appear to be much difference in the pretreatment yields between the two alkylamines.

TABLE 5A

Recovery of glucan and xylan following pretreatment according to Example 5

| Sample 70% EtOH in $H_2O$ (w/v) plus (w/w biomass) | Glucan % recovery in solids | Xylan % recovery in solids | Al lignin content % change | Initial pH |
|---|---|---|---|---|
| 6% MA, 187° C. | 94.6 | 101.3 | −42% | 12.89 |
| 10% MA, 187° C. | 91.2 | 94.1 | −56% | 13.03 |
| 14% MA, 187° C. | 96.8 | 102.3 | −60% | 13.08 |
| 6% DMA, 168° C. | 95.6 | 103.5 | −43% | 12.59 |
| 10% DMA, 168° C. | 98.5 | 106.4 | −48% | 12.71 |
| 14% DMA, 168° C. | 92.3 | 97.1 | −53% | 12.80 |
| 14% DMA, 187° C. | 94.0 | 95.8 | −53% | 12.80 |

Saccharification was performed for 96 h as described in Example 1 except that the Spezyme:Multifect:Novozymes 188 ratio was 6.68:3.34:1.67 mg/g dry solids in the presence of 1% Tween 20 (w/v) at a solids loading of 14% (w/w).

As shown in Table 5B, the MA-pretreated biomass gave higher glucose saccharification yields than did those samples pretreated with DMA. The 10% MA (MW=31) sample should be equivalent to that with 14% DMA (MW=45) in terms of nucleophile concentration yet the glucose yield is higher. The xylose monomer yields for the same concentration were either equivalent or slightly higher with DMA than with MA. There may be a steric advantage to the use of MMA over DMA in the fragmentation of the lignin, giving a slightly greater extent of extraction and a higher saccharification yield.

TABLE 5B

Monomeric glucose and xylose yields following enzymatic saccharification for 96 h, pretreated as described in Example 5

| Sample 70% $EtOH/H_2O$ (w/v) plus (w/w biomass) | Glucose monomer saccharification only (% theoretical yield) | Xylose monomer saccharification only (% theoretical yield) |
|---|---|---|
| 6% MA, 187° C. | 75.82 | 61.02 |
| 10% MA, 187° C. | 78.05 | 71.48 |
| 14% MA, 187° C. | 80.42 | 70.87 |
| 6% DMA, 168° C. | 70.44 | 63.85 |
| 10% DMA, 168° C. | 73.04 | 67.04 |
| 14% DMA, 168° C. | 73.35 | 72.9 |
| 14% DMA, 187° C. | 71.82 | 68.59 |

Example 6

The Effect of Thioglycolate as an Additional Component of the Solvent Solution

The purpose of this Example was to study the effect of organo-mercaptans (e.g., thioglycolate) in the solvent solution. Further, surfactants like Tween 20 often enhance the rate and yield of monomeric sugar release, but at an added cost. It is likely that the surfactant coats any residual lignin, decreasing the non-productive binding of the enzyme to the lignin. A cost-savings could be realized by an improved pretreatment that obviates the need for surfactant in the saccharification step. Such an improvement could be accomplished by further enhancing the extraction of lignin in the pretreatment or by modifying the residual lignin chemically such that less enzyme is lost to lignin adsorption during saccharification.

In this Example, pretreatment was performed as in Example 3 except that the 70% EtOH in $H_2O$ (v/v) solvent in which the bagasse was suspended contained 14% MA with and without 2% thioglycolic acid, 2% glycolic acid or 2% glycine (all w/w biomass). In addition, the pretreatment was performed at 187° C. for 1 h instead of at 168° C. for 140 min.

The subsequent enzymatic saccharification was performed as in Example 5 except that the reaction was performed in the presence and absence of 1% Tween 20 (w/v). FIG. 1A shows lowing pretreatment with 70% EtOH/$H_2O$ (v/v) plus 14% MA (w/w biomass) containing either thioglycolic acid, glycolic acid or glycine indicated that the thioglycolic acid gave a significantly higher saccharification rate and yield than did either glycolic acid or glycine. It was concluded that the —SH group was responsible for the reactivity of the thioglycolic acid. The thioglycolic acid likely reacted with quinone methide intermediates produced in the fragmentation of the lignin under alkaline conditions either by reducing the quinone methide or by doing addition reactions to the quinone methides or by substituting for the α- and/or β-aryl ether components of lignin. These reactions likely promote further fragmentation and extraction of the lignin (FIG. 2). The glycolic acid and glycine were much less reactive or unreactive.

TABLE 6

Glucan and xylan yields following pretreatment and monomeric glucose and xylose yields following enzymatic saccharification with and without Tween 20 according to Example 6

Figure 1B:
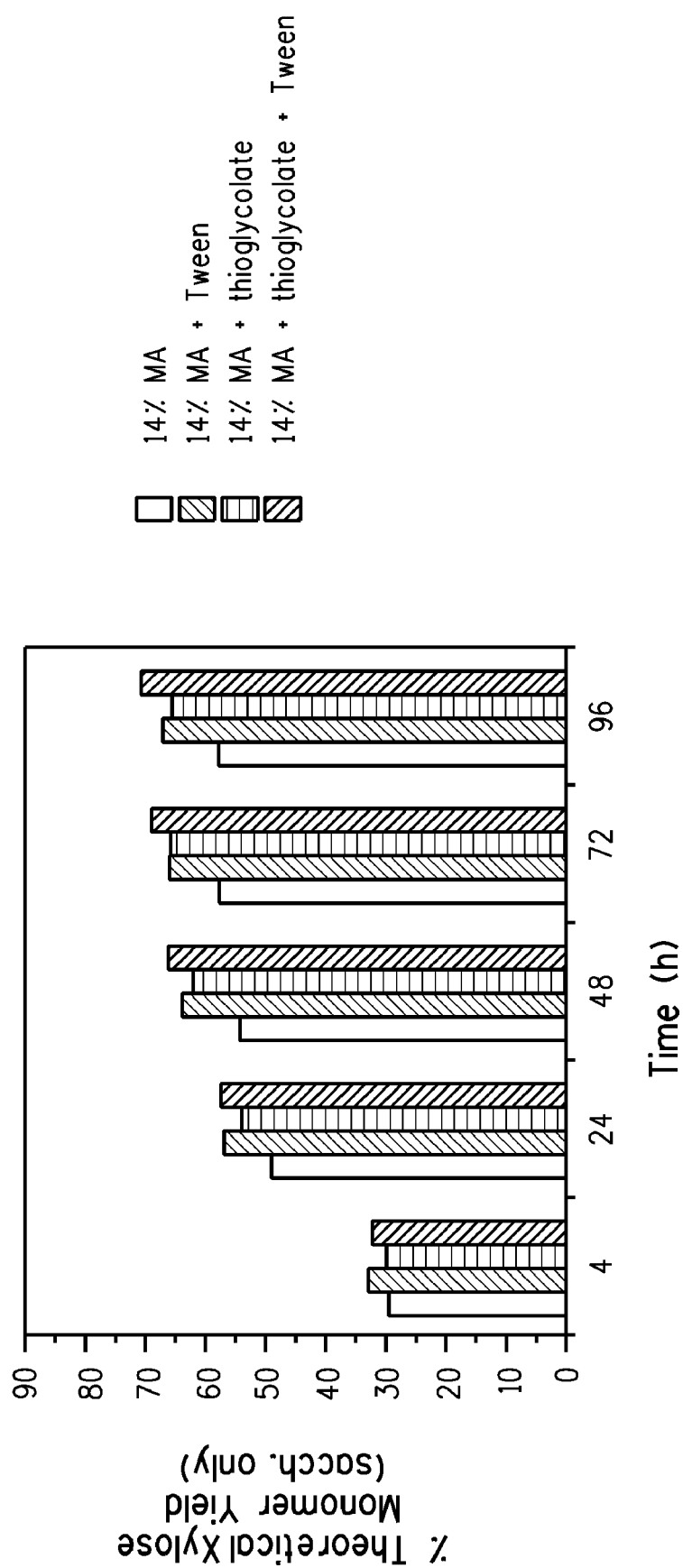

| Sample 70% EtOH/$H_2O$ (w/v) plus (w/w biomass) | % Glucan recovery in solids | % Xylan recovery in solids | Glucose monomer sacch. only (% theoretical yield) without Tween | Xylose monomer sacch. only (% theoretical yield) without Tween | Glucose monomer sacch. only (% theoretical yield) with Tween | Xylose monomer sacch. only (% theoretical yield) with Tween |
|---|---|---|---|---|---|---|
| 14% MA | 96.2 | 104.4 | 69.07 | 58.26 | 75.96 | 67.50 |
| 14% MA + 2% thioglycolic acid | 92.3% | 104.0% | 77.37 | 65.78 | 81.89 | 71.38 |
| 14% MA + 2% glycolic acid | 89.4% | 99.4% | 72.3 | 57.5 | 82.43 | 69.70 |
| 14% MA + 2% glycine | 97.0% | 103.7% | 73.06 | 59.85 | 77.63 | 68.27 | the release of monomeric glucose upon enzymatic saccharification in the presence and absence of Tween following pretreatment at 187° C. for 1 h in 70% EtOH/$H_2O$ and 14% MA with or without 2% thioglycolate. FIG. 1B shows the release of monomeric xylose upon enzymatic saccharification in the presence and absence of Tween following similar pretreatment in the presence and absence of thioglycolate. The addition of 2% thioglycolic acid (w/w biomass) to 70% EtOH/$H_2O$ (v/v) plus 14% MA (w/w biomass) in the pretreatment significantly stimulated the enzymatic saccharification rate and yield of monomeric sugar in the absence of Tween 20. The comparison of the saccharification kinetics in the presence and absence of 1% Tween 20 and with and without 2% thioglycolic acid in the pretreatment (FIGS. 1A and 1B) shows that thioglycolic acid stimulated the saccharification rate and yield to the point where Tween 20 had less influence on both.

In order to understand the nature of the thioglycolic acid chemistry, similar experiments were performed with glycolic acid and glycine in which the —SH of the thioglycolic acid are replaced with —OH and —NH, respectively.

Figure 2A:
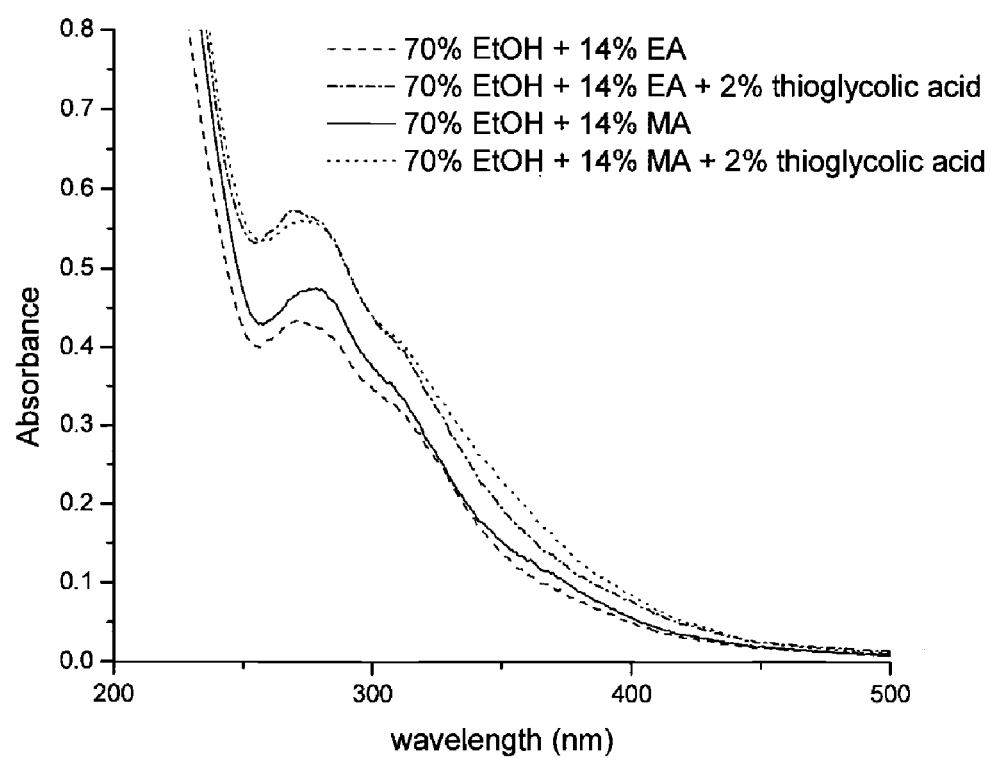
FIGS. 2A and 2B—FIG. 2A shows the UV absorbance spectra of filtrates (diluted 1:5000 with 70% EtOH in $H_2O$ (v/v)) following pretreatment at 187° C. for 1 hour in 70% EtOH in $H_2O$ (v/v) plus 14% methylamine (w/w biomass) and with 14% methylamine (w/w biomass) plus 2% thioglycolic acid (w/w biomass) and in 70% EtOH in $H_2O$ (v/v) plus 14% ethylamine (w/w biomass) and with 14% ethylamine (w/w biomass) plus 2% thioglycolic acid (w/w biomass).
Figure 2B:
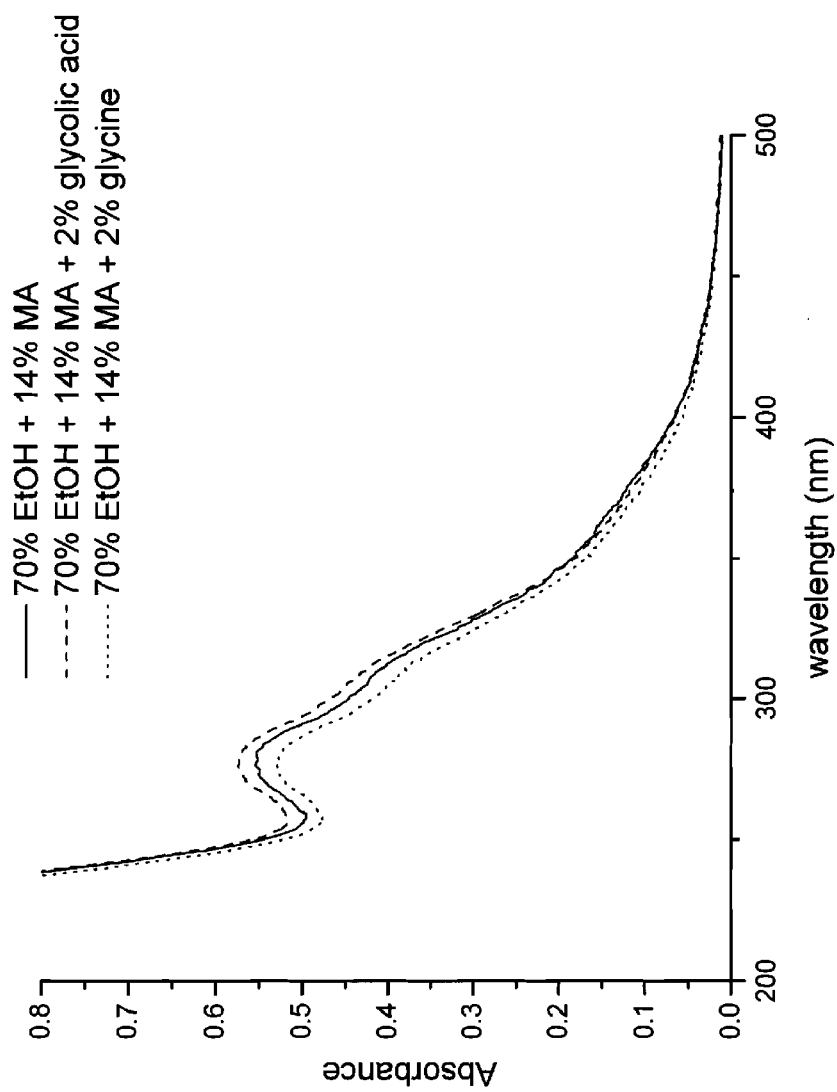

FIG. 2A shows the enhancement by thioglycolic acid of the extraction of lignin (greater UV absorption) in the pretreatment described above (Example 5) in the presence of methylamine. In contrast, there was little difference in the amplitude of the UV spectrum of the biomass treated with 70% EtOH/$H_2O$ (v/v) plus 14% MA (w/w biomass) alone compared to 70% EtOH in $H_2O$ (v/v) plus 14% MA plus 2% glycolic acid or 2% glycine (w/w biomass) (FIG. 2B).

As can be seen in Table 6, the comparison after 96 h of enzymatic saccharification in the absence of Tween 20 fol- Comparison of the HPLC profiles of oligomeric and monomeric sugar during enzymatic saccharification indicated that the addition of thioglycolic acid in the pretreatment (with no Tween in saccharification) produced a very similar profile to that observed after the addition of Tween 20 (with no thioglycolic acid in the pretreatment)—i.e., decreased xylobiose accompanied by increased monomeric xylose and increased cellobiose accompanied by increased monomeric glucose. The monomeric sugar yields for these two conditions were very similar (FIG. 1 and Table 6). These observations are consistent with increased lignin extraction produced by the addition of thioglycolic acid during the pretreatment (see Table 6). It is also possible that there is derivatization of the lignin by the thioglycolic acid to make the residual lignin more hydrophilic (addition of negative charge of carboxylate) resulting in a reduced loss of the cellulose and xylanase enzymes to non-productive binding. Such a decreased impact of lignin on saccharification is similar to what is thought to happen when Tween 20 is added to biomass pretreated in the absence of thioglycolate (i.e., Tween binds to lignin making it more hydrophilic). In summary, the inclusion of 2% thioglycolate (w/w biomass) in the pretreatment with 70% EtOH and alkylamine increased the lignin extraction and stimulated the saccharification yield of both glucose and xylose.

Example 7

Enhancement of Lignin Extraction by Adding Thioglycolate to Methylamine and Ethylamine During Pretreatment Pretreatment was performed as in Example 3 except that the 70% EtOH in $H_2O$ (v/v) solvent in which the bagasse was suspended contained 14% MA or 14% ethylamine (all w/w biomass) with and without 2% thioglycolic acid (w/w biomass). FIG. 2A shows the UV absorbance spectra of filtrates following pretreatment in 70% EtOH plus 14% alkylamine with or without 2% thioglycolate at 187° C. for 1 h. The increase in the UV absorption upon addition of thioglycolic acid to the pretreatment solvent in both cases, indicated that thioglycolic acid enhanced the fragmentation and extraction of lignin, consistent with the decrease of lignin present in the residue following pretreatment, filtration and wash with 70% EtOH in $H_2O$ (v/v).

Example 8

Pretreatment of Biomass Using Ammonium Sulfide During Lignin Extraction

The purpose of this Example was to study the effect of ammonium sulfide on biomass pretreatment. Pretreatment was performed as in Example 3 except that the 70% EtOH/$H_2O$ (v/v) solvent in which the bagasse was suspended contained 14% MA (w/w biomass) plus 2% or 6% $(NH_4)_2S$ (w/w biomass). Enzymatic saccharification was performed as in Example 5. Saccharification yields in the presence and absence of 1% Tween 20 (v/v) at 96 h following pretreatment in 70% EtOH plus 14% MA in the presence and absence of 2% and 6% ammonium sulfide (w/w biomass) are shown in Table 7.

the amount of residual lignin. The presence of 6% $(NH_4)_2S$ in the pretreatment produces an additional boost in the saccharification yield, well above that of the sample saccharified with Tween 20, but pretreated in the absence of $(NH_4)_2S$.

Example 9

Ammonium Sulfide Enhanced Lignin Extraction

Figure 3A:
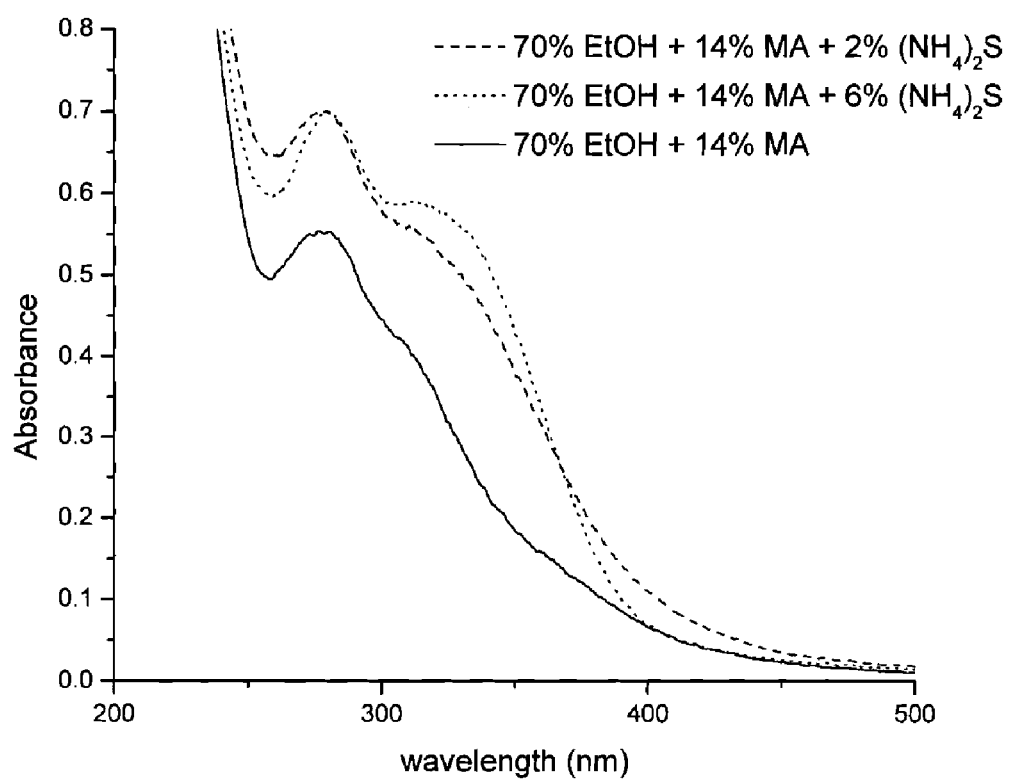
FIGS. 3A and 3B—FIG. 3A shows the UV absorbance spectra of filtrates (diluted 1:5000 with 70% EtOH in $H_2O$ (v/v)) following pretreatment at 187° C. for 1 h in 70% EtOH in $H_2O$ (v/v) plus 14% methylamine (w/w biomass) with or without 2% or 6% $(NH_4)_2S$ (w/w biomass).

Pretreatment was performed as in Example 3 except that the 70% EtOH in $H_2O$ (v/v) solvent in which the bagasse was suspended contained 14% MA (w/w biomass) with no additions and with 2% or 6% $(NH_4)_2S$ (w/w biomass). FIG. 3A shows the absorbance spectra of the filtrates following pretreatment, diluted 5000-fold with 70% EtOH in $H_2O$ (v/v). The addition of 2% and 6% $(NH_4)_2S$ to the 70% EtOH/$H_2O$ plus MA showed a very large enhancement in the UV absorption of the filtrate following pretreatment, indicating an increase in the extracted lignin. The enhancement of the lignin extraction by inclusion of $(NH_4)_2S$ in the pretreatment is consistent with the significant enhancement of the subsequent enzymatic saccharification (Table 7).

Example 10

Pretreatment of Biomass Using Elemental Sulfur During Lignin Extraction

The purpose of the Example was to study the effect of elemental sulfur in biomass pretreatment. Consequently,

TABLE 7

Yields of glucan and xylan following pretreatment according to Example 8

| Sample | % Glucan recovery in solids | % Xylan recovery in solids | Glucose monomer sacch. only (% theoretical yield) no Tween | Xylose monomer sacch. only (% theoretical yield) no Tween | Glucose monomer sacch. only (% theoretical yield) with Tween | Xylose monomer sacch. only (% theoretical yield) with Tween |
|---|---|---|---|---|---|---|
| 14% MA | 90.60 | 97.52 | 69.07 | 58.26 | 75.96 | 67.5 |
| 14% MA + 2% $(NH_4)_2S$ | 91.62 | 98.03 | 78.9 | 68.68 | 84.79 | 76.39 |
| 14% MA + 6% $(NH_4)_2S$ | 87.02 | 92.43 | 84.2 | 73 | 90.87 | 83.23 |

Figure 3B:
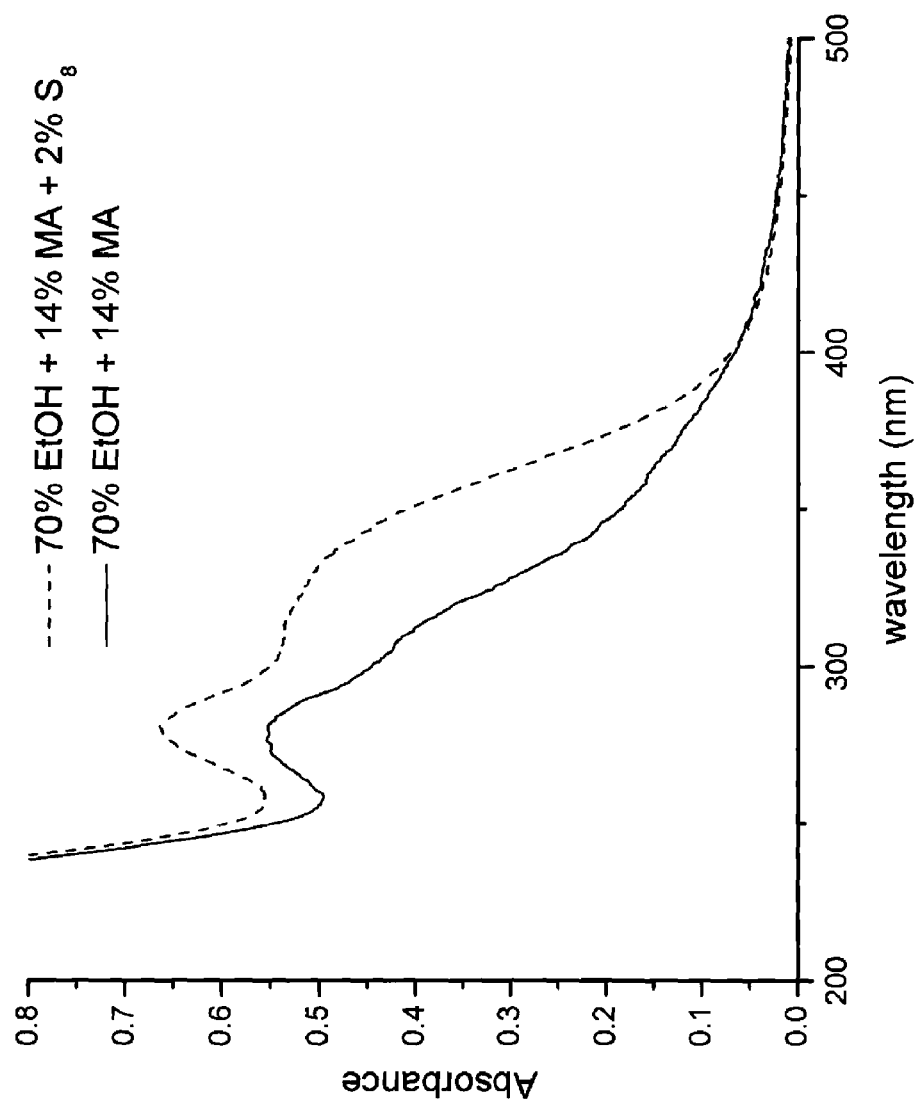

The comparison of the enzymatic saccharifications in the absence of Tween 20 following pretreatment with 70% EtOH in $H_2O$ (v/v) plus 14% MA (w/w biomass) containing either 0%, 2% or 6% $(NH_4)_2S$ (w/w biomass) showed that $(NH_4)_2S$ when present in the pretreatment promoted subsequent enzymatic saccharification. The enhanced saccharification was likely associated with an increased fragmentation and extraction of the lignin (FIG. 3). Table 7 shows that the effect of the 2% $(NH_4)_2S$ pretreatment was quite marked for the saccharification of xylan to xylose and for glucan to glucose. The HPLC analyses of the hydrolysates indicated, as in the case of thioglycolic acid, that the enhanced extraction of the lignin by $(NH_4)_2S$ in the pretreatment with no surfactant in the saccharification behaved similarly to the addition of surfactant in the saccharification but without $(NH_4)_2S$ in the pretreatment. The surfactant coats the residual lignin while the $(NH_4)_2S$ reduces elemental sulfur was either added or not to the biomass at a concentration equal to 1% or 2% of the weight of the biomass. The pretreatment was performed as in Example 3 except that the biomass with and without sulfur was suspended in 70% EtOH in $H_2O$ v/v containing 14% MA (w/w biomass). The suspensions were placed in pressure vessels as in Example 3 and heated to 187° C. for 1 h. After rapid cooling of the pressure vessels to room temperature, the contents were filtered and washed with 70% EtOH in $H_2O$ (v/v) and left to air dry. The filtrate obtained after the pretreatment at 2% sulfur was diluted 1:5000 with 70% EtOH in $H_2O$ (v/v) and the UV spectrum was recorded. As shown in FIG. 3B, there is a substantial enhancement in the UV absorbance in the presence of 14% MA (w/w biomass) plus 2% sulfur (w/w biomass) as compared to the 14% MA (w/w biomass) alone in 70% EtOH in $H_2O$ (v/v). The increased extraction of lignin in the presence of sulfur is consistent with the decreased content of lignin in the solids following pretreatment and the enhanced monomeric sugar yield following enzymatic saccharification (Table 8).

The subsequent enzymatic saccharifications were carried out as in Example 5 on the sample containing 1% sulfur except that they were performed in either the presence or absence of 1% Tween 20 (w/v) in the case of the sample without sulfur and in the presence and absence of 0.5% PEG 2000 (w/w biomass) in the case of the sample with sulfur. Parallel experiments (not shown) have indicated that 1% Tween 20 (w/v) and 0.5% PEG 2000 (w/w biomass) give virtually the same degree of enhancement to the enzymatic saccharification. Pretreatment yields and enzymatic saccharification yields in the presence and absence of 1% Tween 20 (v/v) at 96 h following pretreatment in 70% EtOH plus 14% MA and in the presence and absence of 0.5% PEG 2000 (w/w biomass) and 1% S (w/w biomass) are shown in Table 8.

TABLE 8

Yields of glucan and xylan following pretreatment according to Example 10 and yields of monomeric sugars following enzymatic saccharification

| Sample | % Glucan recovery in solids | % Xylan recovery in solids | Al lignin (% content change) | Monomeric glucose (% of theoretical yield) | Monomeric xylose (% of theoretical yield) |
|---|---|---|---|---|---|
| 70% EtOH, 14% MA | 99.22 | 102.95 | −51 | 71.8 | 59.1 |
| 70% EtOH, 14% MA + 1% Tween 20 (v/v) | 99.22 | 102.95 | −51 | 78.0 | 68.1 |
| 70% EtOH, 14% MA + 1% S | 97.58 | 100.42 | −77 | 86.0 | 82.8 |
| 70% EtOH, 14% MA + 1% S + 0.5% PEG 2000 | 97.58 | 100.42 | −77 | 88.1 | 84.2 |

The addition to the biomass of 1% (w/w biomass) of elemental sulfur produces a substantial increase in the enzymatic saccharification yield of glucose and xylose, both in the presence and in the absence of surfactant. The presence of the sulfur, in addition to increasing the sugar yields, modifies the residual lignin to the point where the addition of PEG 2000 produces only a very small increase in the enzymatic sugar yield.

Example 11

Effect of Addition of Ammonia to Organic Solvent Solution Pretreatment Containing Methylamine and Elemental Sulfur Pretreatment was performed as in Example 3 except that the bagasse contained 1% elemental sulfur (w/w biomass) and was suspended in 70% EtOH in $H_2O$ (v/v) plus either 14% MA (methylamine), 7% $NH_3$+7% MA, 10% $NH_3$+4% MA, or 14% $NH_3$ (all w/w biomass). The samples were heated at 187° C. for 1 h in pressure vessels and then rapidly cooled to room temperature in water bath. The residue was filtered, washed and dried as previously described. Enzymatic saccharification was performed as in Example 5, but in the presence and absence of 0.5% PEG 2000 (w/w biomass).

TABLE 9

The yield of monomeric sugars following treatment described in Example 11

| Sample 70% EtOH in $H_2O$ (v/v) + 1% S (w/w biomass) + additives (w/w biomass) | % Glucan recovery in solids | % Xylan recovery in solids | Monomeric glucose (% of theoretical yield) without PEG | Monomeric xylose (% of theoretical yield) without PEG | Monomeric glucose (% of theoretical yield) with PEG | Monomeric xylose (% of theoretical yield) with PEG |
|---|---|---|---|---|---|---|
| 14% MA | 96.8 | 102.3 | 83.3 | 74.6 | 85.8 | 75.8 |
| 7% $NH_3$ + 7% MA | 90.80 | 96.98 | 79.5 | 68.2 | 82.9 | 71.1 |
| 10% $NH_3$ + 4% MA | 91.61 | 97.35 | 76.2 | 66.4 | 80.8 | 68.7 |
| 14% $NH_3$ | 95.24 | 100.41 | 66.71 | 59.5 | 74.3 | 63.9 |

As indicated in Table 9, replacement of methylamine with ammonia does not have an impact on the glucan and xylan recovery upon pretreatment. The saccharification yields for both monomeric glucose and xylose, however, decrease progressively the more extensive the replacement of methylamine with ammonia (Table 9). The differences between the saccharification runs with and without PEG 2000 are for the most part only a few percent. An economic analysis of the overall process is required to determine whether there is a savings in the cost of sugar production upon either the replacement of methylamine with ammonia in the pretreatment, despite the loss in yield, or upon addition of PEG 2000 in the saccharification, despite the cost of the additive.

Example 12

Organic Solvent Solution Pretreatment of Corn Cob, Switchgrass and Sugar Cane Bagasse Using Methylamine and Elemental Sulfur The organic solvent solution plus methylamine plus elemental sulfur pretreatment was tested on three different feedstocks using conditions similar to those of Example 10 except that the biomass was mixed with 1% elemental sulfur (w/w biomass) in all cases and suspended in 70% EtOH in $H_2O$ containing 14% methylamine (w/w biomass). Switchgrass and sugar cane bagasse were heated at 183° C. for 1 h. Corn cob was heated at 187° C. for 1 h. The samples were washed with 70% EtOH in $H_2O$ (v/v) and air-dried as in Example 10 and then saccharified as described in Example 5 except that the saccharifications were performed in the presence and absence of PEG 2000 (0.5 wt % of biomass). The monomeric sugar yields are shown in Table 10.

TABLE 10

The yield of monomeric sugars following treatment described in Example 12

| sample | Glucose monomer, sacch. only (% of theoretical yield) without PEG | Glucose monomer, sacch. only (% of theoretical yield) with PEG | Xylose monomer, sacch. only (% of theoretical yield) without PEG | Xylose monomer, sacch. only (% of theoretical yield) with PEG |
|---|---|---|---|---|
| Corn cob, 187° C. | 81.99 | 82.67 | 39.06 | 47.65 |
| Switchgrass, 183° C. | 82.06 | 82.95 | 43.58 | 59.26 |
| Bagasse, 183° C. | 79.84 | 80.5 | 68.51 | 70.92 |

The monomeric glucose yields differ very little between the different feedstocks (e.g., corn, switchgrass and bagasses) and there is little effect of the addition of PEG 2000. The overall oligomer plus monomer xylose yields were similar for the three feedstocks, but the ratio of monomer to oligomer differed appreciably, with bagasse giving the highest monomer/oligomer ratio and corn cob the least. The extent of monomer formation increased somewhat for cob and switchgrass with the addition of PEG, but very little for bagasse. It is likely that structural differences between the xylose oligomers, solubilized in the different feedstocks, account for the differences in their enzymatic conversion to monomer and not the efficacy of the pretreatment.

These results demonstrate the range of applicability of the developed pretreatment to feedstocks that differ appreciably in their lignin composition—corn cob, switchgrass and bagasse ~14%, 23% and ~25%, respectively, of DM.

Example 13

Comparison of Enzymatic Saccharification of Corn Cob, Pretreated Using Organic Solvent Solution in the Presence of Methylamine and Sulfur, to Corn Cob Pretreated with Dilute Ammonia and to Untreated Corn Cob Organic Solvent Solution Pretreatment Using Elemental Sulfur and Methylamine Two batches of 134 g (8.4% moisture content) hammermilled corn cob, one with 0.5% and the other with 1% elemental sulfur (w/w biomass), were each suspended in 280 mL EtOH, 66.7 mL water, 53.3 mL methylamine solution (47.4 g) and heated to 195° C. for 1 h at temperature with mechanical stirring in a 1 L pressure vessel. Each batch was then washed with 70% EtOH in $H_2O$ (v/v) 3 times. The material was air dried and the two batches were pooled.

Dilute Ammonia Pretreatment:

To 713 g (5.8% moisture content) of hammermilled corncob loaded into a 5 L reactor, 138.9 g of $NH_4OH$ solution (29 wt % $NH_3$) and 491.1 g additional water were added to give a 50% solids loading. The reactor was heated to 140° C. for 20 min at temperature. The $NH_3$ was then flashed off while the reactor cooled and was then further removed by vacuum. The contents of the reactor were removed and used for saccharification.

Untreated Biomass:

Untreated (8.4% moisture content) hammermilled corn cob was used as a control for this saccharification study.

Glucan and xylan contents were determined by using the NREL procedure (see Example 1). Analysis of hydrolyzed sugars was done by HPLC (using the method described above with the exception that the column temp was 65° C. instead of 60° C.). Saccharification of this material was done in a 1 L glass Erlenmeyer flask (Chemglass, Vineland, N.J.) on a rotary shaker set to 200 rpm and 48° C. In the comparative saccharifications, 75 mmol sodium citrate buffer at average pH of 5.4-5.6 was used to control the pH. In addition, 5 ppm each of penicillin and virginiamycin antibiotics were added to inhibit bacterial growth and 0.5% PEG 2000 (wt % of solids) was added to decrease enzyme adsorption to lignin. The solids were loaded based on their carbohydrate content, which was 18.3 wt % carbohydrate ((glucan+xylan)/(glucan+xylan+mass of liquid added to biomass)). This corresponded to a solids loading of 20.8%, 25.2% and 25.6% for the organic solvent solution, dilute ammonia and untreated material, respectively. The enzymes used were described in Example 1. The protein weight ratio of Spezyme:Novozyme 188 was 4:1 and the loading of total Spezyme/Novozyme 188 protein was 37.5, 25 and 10 mg protein/g of glucan for the high, medium and low enzyme loadings, respectively. Multifect was loaded at 15, 10 and 4 mg/g of xylan for the high, medium and low enzyme loadings, respectively. The buffer, additional water, enzymes, surfactant and antibiotics were mixed together in a 1 L flask and then the first 60% of the solids were added. The flasks were heated and shaken. After 1 h, the next 20% of solids was added to each flask. The final 20% of solids was added 3 h later. The reactions continued to mix at temperature for a total of 96 h after which point they were removed. A representative sample of each was transferred to a centrifuge vessel, spun in the centrifuge and the liquid fraction was decanted. The solid was resuspended in water, recentrifuged and the liquid separated was again decanted. This was repeated four additional times. The liquid was analyzed for monomer content using the HPLC. The oligomer content was determined by hydrolyzing for 1 h at 121° C. a portion of this wash fraction with sulfuric acid (4% w/v), reanalyzing on the HPLC and the difference with the monomer content was considered to be derived from the oligomers. The monomer and oligomer content produced by enzymatic saccharification is reported as a yield of the initial amount of glucan and/or xylan in the initial solids in the flasks. Results of these experiments are shown in Table 11 below.

TABLE 11

Sugar yield from various types of pretreatments as described in Example 13

| Pretreatment | Enzyme Loading | % glucose yield (mono) | % xylose yield (mono) | % glucan converted to glucose oligomers | % xylan converted to xylose oligomers | % glucose yield from sacch (mono + oligo) | % xylose yield from sacch (mono + oligo) | % glucose + Xylose yield from sacch (mono + oligo) |
|---|---|---|---|---|---|---|---|---|
| EtOH/MA/$S_8$ | High | 80% | 62% | 13% | 39% | 95% | 102% | 98% |
| Dilute $NH_3$ | High | 60% | 42% | 9% | 38% | 71% | 80% | 75% |
| Untreated | High | 24% | 17% | 3% | 4% | 25% | 20% | 23% |
| EtOH/MA/$S_8$ | Medium | 72% | 55% | 10% | 42% | 84% | 97% | 90% |
| Dilute $NH_3$ | Medium | 51% | 36% | 8% | 38% | 60% | 74% | 66% |
| Untreated | Medium | 24% | 17% | 3% | 4% | 26% | 20% | 23% |
| EtOH/MA/$S_8$ | Low | 45% | 39% | 5% | 54% | 52% | 94% | 70% |
| Dilute $NH_3$ | Low | 35% | 25% | 7% | 42% | 43% | 68% | 54% |
| Untreated | Low | 19% | 14% | 2% | 2% | 21% | 16% | 19% |

This comparative study demonstrates the efficacy of the organic solvent solution/methylamine/sulfur pretreatment in enhancing the saccharification of pretreated corn cob relative to the dilute ammonia process and to no pretreatment at solids loadings (20.8% w/w for organic solvent solution) in the saccharifier, considerably higher than in the earlier examples (14% w/w). The enzymatic conversion to monomer plus oligomer following the organic solvent solution pretreatment is nearly quantitative at the high enzyme loading. Under all enzyme loadings, the organic solvent solution pretreatment gives the highest conversion to monomer glucose and xylose and to monomer plus oligomer glucose and xylose.

Example 14

Comparison of Performance on Various Feedstocks of Organic Solvent Pretreatment in the Presence of Methylamine and Elemental Sulfur To compare the effect of organic solvent pretreatment with methylamine (MA) and sulfur (S) on five feedstocks, differing in their lignin content, corn cob (AI lignin 14% of dry matter (DM), switchgrass (AI lignin 23.4% of DM), sugar cane bagasse AI (lignin 25% of DM), sugar cane straw (AI lignin 25% of DM) and yellow poplar (AI lignin 20% of DM) were treated in 70% ethanol in water (v/v) containing 10 or 14% MA and elemental S using the conditions detailed in Table 1. The pretreated biomass was then washed, dried and subjected to enzymatic saccharification. Prior to pretreatment, all feedstocks were first milled in a knife mill using a 1 mm sieve. The pretreatments were performed at the indicated solids loadings in 70% EtOH in water (v/v) containing MA and S and heated at the indicated temperatures and duration. The samples were filtered and then washed with 70% EtOH and then allowed to air dry at ambient temperature. The glucan and xylan contents and percent recoveries following the pretreatment are summarized in Table 12. The samples were then saccharified at 48° C. using Spezyme CP:Mutifect Xylanase:Novozyme 188 at a ratio of 6.68:3.34:1.67 mg/g biomass at a solids loading of 14% in 50 mM NaCitrate, pH 4.7 and at the indicated enzyme loadings for the other solids loadings in 50 mM NaCitrate, pH 4.8-4.9. Saccharifications were performed for the indicated times. The monomeric sugar yields were determined by HPLC (BioRad HPX-87H column at 60° C., 0.01 N $H_2SO_4$ mobile phase) as indicated in Example 1 and are based on the sugar content of the pretreated biomass going into the saccharifier. The total sugar concentration (oligomer plus monomer) was determined by taking the supernatant at the end of saccharification and autoclaving for 1 h at 121° C. in 4% $H_2SO_4$ followed by HPLC analysis. The saccharification results are shown in Table 13.

These results show that pretreatment of lignocellulosic biomass with organic solvent, containing methylamine and sulfur, gives treated biomass with a highly conserved and enriched glucan and xylan content across a broad range of feedstocks, differing appreciably in their lignin content. In addition, this pretreatment facilitates the subsequent enzymatic saccharification, giving high yields of soluble sugars for the same collection of feedstocks.

TABLE 12

Glucan and xylan content and recovery following pretreatment, washing and air-drying

| Sample | Glucan content (% of dry matter) | Xylan content (% of dry matter) | % Glucan recovery following pretreatment | % Xylan recovery following pretreatment |
|---|---|---|---|---|
| Corn cob, 195° C., 1 h, 70% EtOH (v/v), 14% MA, 0.75% S (wt/wt biomass), washed with 70% EtOH (v/v) and air-dried | 53 | 38 | 97 | 100 |
| Switchgrass, solids loading 18%, 180° C., 1 h, 70% EtOH (v/v), 14% MA, 1% S (wt/wt biomass), washed with 70% EtOH (v/v) and air-dried | 50 | 36 | 93 | 95 |

TABLE 12-continued

Glucan and xylan content and recovery following pretreatment, washing and air-drying

| Sample | Glucan content (% of dry matter) | Xylan content (% of dry matter) | % Glucan recovery following pretreatment | % Xylan recovery following pretreatment |
| --- | --- | --- | --- | --- |
| Sugar cane bagasse, solids loading 11%, 180° C., 1 h, 70% EtOH (v/v), 14% MA, 1% S (wt/wt biomass), washed with 70% EtOH (v/v) and air-dried | 50 | 33 | 93 | 100 |
| Sugar cane straw,, solids loading 26%, 188° C., 1 h, 70% EtOH (v/v), 14% MA, 1% S (wt/wt biomass), washed with 70% EtOH (v/v) and air-dried | 44 | 29 | 87 | 88 |
| Yellow poplar, solids loading 26%, 200° C., 1 h, 70% EtOH (v/v), 14% MA, 1% S (wt/wt biomass), washed with 70% EtOH (v/v) and air-dried | 67 | 26 | 100 | 89 |

TABLE 13

Conversion of glucan and xylan to glucose and xylose, respectively, by enzymatic saccharification

| Sample | Monomeric Glucose (% theoretical yield) | Monomeric Xylose (% theoretical yield) | Glucose monomer + soluble oligomer (% theoretical yield) | Xylose monomer + soluble oligomer (% theoretical yield) |
| --- | --- | --- | --- | --- |
| Corn cob, solids loading 26%, 190° C., 1 h, 70% EtOH (v/v), 10% MA, 1% S (wt/wt biomass), saccharification 168 h, 14% solids, + 0.5% PEG 2000 (wt/wt biomass) | 92.5 | 54 | | |
| Corn cob, solids loading 26%, 195° C., 1 h, 70% EtOH (v/v), 14% MA, 0.75% S (wt/wt biomass), saccharification 96 h, 18.5% carbohydrate loading, Spe + Novo 188 (37.5 mg/g glucan), Multifect 15 mg/g xylan | 78 | 59 | 92 | 96 |
| Switchgrass, solids loading 26%, 180° C., 1 h, 70% EtOH (v/v), 14% MA, 1% S (wt/wt biomass), saccharification 168 h, 14% solids + 0.5% PEG 2000 (wt/wt biomass) | 92 | 68 | | |
| Switchgrass, solids loading 18%, 180° C., 1 h, 70% EtOH (v/v), 14% MA, 1% S (wt/wt biomass), saccharification 96 h, 15% carbohydrate loading, Spe + Novo 188 (37.5 mg/g glucan), Multifect 15 mg/g xylan | 71 | 49 | 78 | 89 |
| Sugar cane bagasse, solids loading 26%, 180° C., 1 h, 70% EtOH (v/v), 14% MA, 1% S (wt/wt biomass), saccharification 168 h, 14% solids | 89 | 85 | | |
| Sugar cane bagasse, solids loading 11%, 180° C., 1 h, 70% EtOH (v/v), 14% MA, 1% S (wt/wt biomass), saccharification 96 h, 11.5% carbohydrate loading, Spe + Novo 188 (37.5 mg/g glucan), Multifect 15 mg/g xylan | 89 | 53 | 95 | 92 |

TABLE 13-continued

Conversion of glucan and xylan to glucose and xylose, respectively, by enzymatic saccharification

| Sample | Monomeric Glucose (% theoretical yield) | Monomeric Xylose (% theoretical yield) | Glucose monomer + soluble oligomer (% theoretical yield) | Xylose monomer + soluble oligomer (% theoretical yield) |
|---|---|---|---|---|
| Sugar cane straw, solids loading 26%, 188° C., 1 h, 70% EtOH (v/v), 14% MA, 1% S (wt/wt biomass), saccharification 144 h, 14% solids, + 0.5% PEG 2000 (wt/wt biomass) | 95 | 67 | | |
| Yellow poplar, solids loading 26%, 200° C., 1 h, 70% EtOH (v/v), 14% MA, 1% S (wt/wt biomass), saccharification 168 h, 14% solids, + 0.5% PEG 2000 (wt/wt biomass) | 90 | 60 | 100 | 91 |

What is claimed is:

1. A method for producing fermentable sugars comprising:
   (a) providing lignocellulosic biomass comprising lignin;
   (b) suspending the biomass of (a) in an organic solvent solution comprising water and one or more alkylamines under alkaline conditions whereby a biomass-solvent suspension is formed;
   (c) heating the biomass-solvent suspension to a temperature of about 100° C. to about 220° C. for about 5 minutes to about 5 hours whereby lignin is fragmented and is dissolved in the suspension;
   (d) filtering free liquid under pressure whereby the dissolved lignin is removed and whereby carbohydrate-enriched biomass is produced;
   (e) optionally washing the carbohydrate-enriched biomass of (d) with an organic solvent solution producing a solvent-washed carbohydrate-enriched biomass;
   (f) removing solvent from the carbohydrate-enriched biomass of (e), or of (d) when (e) is omitted;
      wherein a readily saccharifiable carbohydrate-enriched biomass is produced; and
   (g) contacting the readily saccharifiable carbohydrate-enriched biomass of (f) with an enzyme consortium, whereby fermentable sugars are produced.

2. The method of claim 1 wherein removing solvent is by washing with water or drying.

3. The method of claim 1 wherein step (e) is repeated one or more times.

4. The method of claim 1 wherein the heating step of (c) occurs in a sealed pressure vessel.

5. The method of claim 1 wherein the filtering step of (d) occurs under pressure.

6. The method of claim 1 wherein the one or more alkylamines is selected from the group consisting of R—$NH_2$, $R_2$—NH, $R_3$N, ($H_2$N—R—$NH_2$), ($H_2$N—R($NH_2$)$_2$), (HO—R—$NH_2$), ((HO)$_2$—R—$NH_2$), (HO—R—($NH_2$)$_2$), (HS—R—$NH_2$), ((HS)$_2$—R—$NH_2$), (HS—R—($NH_2$)$_2$) and ($H_2$N—R(OH)(SH)) and combinations thereof, wherein R is independently a monovalent, divalent or trivalent 1-6 carbon alkane, alkene or alkyne, linear, cyclic or branched.

7. The method of claim 6 wherein R is independently methyl, ethyl, propyl or butyl.

8. The method of claim 6 wherein the alkylamine is methylamine.

9. The method of claim 6 wherein the alkylamine is at a concentration from about 1% to about 20% by weight of dry biomass.

10. The method of claim 1 wherein the organic solvent solution to biomass in step (b) has a weight ratio of about 10 to 1 to 0.5 to 1.

11. The method of claim 1, wherein the heated suspension of step (c) is cooled to room temperature before filtering in step (d).

12. The method of claim 1 wherein the biomass is selected from the group consisting of switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

13. The method of claim 1 wherein the organic solvent solution of (b) further comprises one or more additional components selected from the group consisting of alkali or alkaline earth hydroxides or carbonates, ammonia, thiols, polysulfides or sulfides or combinations thereof.

14. The method of claim 1 wherein the organic solvent solution of (b), and any unreacted alkylamine or other unreacted components are recyclable.

15. The method of claim 1 wherein the organic solvent solution of (b) and the organic solvent solution of (e) independently comprise a solvent selected from the group consisting of alcohols, diols, and aprotic solvents.

16. The method of claim 15 wherein the organic solvent solution comprises a solvent selected from the group consisting of methanol, ethanol, propanol, butanol, pentanol and hexanol, isomers thereof, and diols thereof.

17. The method of claim 16 wherein the organic solvent solution comprises from about 40% to about 70% ethanol in water.

18. The method of claim 1 wherein the lignocellulosic biomass of step (a) has a carbohydrate content that is highly conserved through steps (a) through (d).

19. A method for producing fermentable sugars comprising:
   (a) providing lignocellulosic biomass comprising lignin;
   (b) suspending the biomass of (a) in an organic solvent solution comprising water and one or more alkylamines under alkaline conditions whereby a biomass-solvent suspension is formed;

(c) heating the biomass-solvent suspension to a temperature of about 100° C. to about 220° C. for about 5 minutes to about 5 hours whereby lignin is fragmented and is dissolved in the suspension;
(d) filtering free liquid under pressure whereby the dissolved lignin is removed and whereby carbohydrate-enriched biomass is produced;
(e) optionally washing the carbohydrate-enriched biomass of (d) with an organic solvent solution producing a solvent-washed carbohydrate-enriched biomass;
(f) removing solvent from the carbohydrate-enriched biomass of (e), or of (d) when (e) is omitted;
    wherein a readily saccharifiable carbohydrate-enriched biomass is produced;
(g) contacting the readily saccharifiable carbohydrate-enriched biomass of (f) with an enzyme consortium, whereby fermentable sugars are produced.

* * * * *